(12) United States Patent
Ghidini

(10) Patent No.: US 9,469,669 B2
(45) Date of Patent: *Oct. 18, 2016

(54) ISOXAZOLIDINE DERIVATIVES

(71) Applicant: Chiesi Farmaceutici S.p.A., Parma (IT)

(72) Inventor: Eleonora Ghidini, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,156

(22) Filed: Sep. 3, 2015

(65) Prior Publication Data

US 2015/0376226 A1 Dec. 31, 2015

Related U.S. Application Data

(62) Division of application No. 13/964,298, filed on Aug. 12, 2013, now Pat. No. 9,155,747.

(30) Foreign Application Priority Data

Sep. 13, 2012 (EP) .................................... 12184286

(51) Int. Cl.
*A61K 31/58* (2006.01)
*A61M 11/00* (2006.01)
*A61M 15/00* (2006.01)
*A61K 45/06* (2006.01)
*C07J 71/00* (2006.01)

(52) U.S. Cl.
CPC ............ *C07J 71/0068* (2013.01); *A61K 31/58* (2013.01); *A61K 45/06* (2013.01); *A61M 11/00* (2013.01); *A61M 15/0028* (2013.01)

(58) Field of Classification Search
USPC .................................................. 514/171, 176
See application file for complete search history.

(56) References Cited

U.S. PATENT DOCUMENTS

| 8,481,517 | B2 | 7/2013 | Ghidini et al. |
| 2011/0065678 | A1 | 3/2011 | Armani et al. |
| 2012/0234316 | A1 | 9/2012 | Ghidini et al. |
| 2012/0238531 | A1 | 9/2012 | Ghidini et al. |
| 2013/0035320 | A1 | 2/2013 | Ghidini et al. |
| 2015/0057257 | A1 | 2/2015 | Ghidini et al. |

FOREIGN PATENT DOCUMENTS

WO  2011/029547  3/2011

OTHER PUBLICATIONS

European Search Report in Application No. 12184286.8 issued Jan. 14, 2013.

*Primary Examiner* — Kathrien Cruz
(74) *Attorney, Agent, or Firm* — Oblon, McClelland, Maier & Neustadt, L.L.P.

(57) ABSTRACT

Glucocorticosteroids that are derivatives of isoxazolidine are useful as anti-inflammatory and antiallergic compounds of the glucocorticosteroid series.

5 Claims, No Drawings

ISOXAZOLIDINE DERIVATIVES

CROSS REFERENCES TO RELATED APPLICATIONS

This application is a divisional application of U.S. patent application Ser. No. 13/964,298filed Aug. 12, 2013, which claims priority to European Patent Application No. 12184286.8, filed on Sep. 13, 2012, which is incorporated herein by reference in its entirety.

BACKGROUND OF THE INVENTION

1. Field of the Invention

The present invention relates to novel anti-inflammatory and antiallergic compounds of the glucocorticosteroid series, methods of preparing such compounds, pharmaceutical compositions comprising such a compound, combinations containing such a compound, and therapeutic uses of such a compound. More particularly, the present invention relates to glucocorticosteroids that are isoxazolidine derivatives.

2. Discussion of the Background

Corticosteroids are potent anti-inflammatory agents, able to decrease the number, activity and movement of inflammatory cells. Corticosteroids are commonly used to treat a wide range of chronic and acute inflammatory conditions including asthma, chronic obstructive pulmonary disease (COPD), allergic rhinitis, rheumatoid arthritis, inflammatory bowel disease and autoimmune diseases. Corticosteroids mediate their effects through the glucocorticoid receptor (GR). The binding of corticosteroids to GR induces its nuclear translocation which, in turn, affects a number of downstream pathways via DNA-binding-dependent (e.g. transactivation) and -independent (e.g. transespression) mechanisms.

Corticosteroids for treating chronic inflammatory conditions in the lung such as asthma and COPD are currently administered through inhalation. One of the advantages of employing inhaled corticosteroids (ICS) is the possibility of delivering the drug directly at site of action, thereby limiting systemic side-effects, thus resulting in a more rapid clinical response and a higher therapeutic ratio.

Although ICS treatment can afford important benefits, especially in asthma, it is important to minimize ICS systemic exposure which leads to the occurrence and severity of unwanted side effects that may be associated with chronic administration. Moreover, the limited duration of action of ICS currently available in the clinical practice contributes to suboptimal management of the disease. While the inhaler technology is the key point to target the lung, the modulation of the substituents on the corticosteroids molecular scaffold is important for the optimization of pharmacokinetic and pharmacodynamic properties in order to decrease oral bioavailability, confine pharmacological activity only in the lung (prodrugs and soft drugs) and increase systemic clearance. Moreover, long lasting ICS activity in the lung is highly desirable as once daily administration of ICS would allow the reduction of the frequency of administration and, thus, substantially improve patient compliance and, as a result, disease management and control. In sum, there is a pressing medical need for developing ICS with improved pharmacokinetic and pharmacodynamic characteristics.

Glucocorticoids isoxazolidine derivatives are for instance described in WO 2006/005611, GB 1578446 and in "Synthesis and topical anti-inflammatory activity of some steroidal [16α,17α-d]isoxazolidines" (J. Med. Chem., 25, 1492-1495, 1982), all of which are incorporated herein by reference in their entireties. Some glucocorticoid isoxazolidine derivatives are also described in the co-pending patent applications WO 2011/029547, WO 2012/123482, and WO 2012/123493, all of which are incorporated herein by reference in their entireties.

However, there remains a need for glucocorticosteroid with improved pharmacological properties.

SUMMARY OF THE INVENTION

Accordingly, it is one object of the present invention to provide novel anti-inflammatory and antiallergic compounds of the glucocorticosteroid series.

It is another object of the present invention to provide novel processes for the preparation of such compounds.

It is another object of the present invention to provide novel compositions which comprising such a compound.

It is another object of the present invention to provide novel methods of treating certain diseases and conditions by administering such a compound.

It is another object of the present invention to provide novel combinations of such a compound with another pharmaceutical active ingredient for the treatment of respiratory disorders, such as beta2-agonists, antimuscarinic agents, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), antitussive agents, mucus regulators, mucolytics, expectorant/mucokinetic modulators, peptide mucolytics, antibiotics, inhibitors of JAK, SYK inhibitors, inhibitors of PI3Kdelta or PI3Kgamma, M3-antagonists/beta2-agonists (MABA), and M3-antagonists/PDE4-inhibitors (MAPI).

These and other objects, which will become apparent during the following detailed description, have been achieved by the inventors' discovery that compounds of formula (I) and salts thereof are useful as anti-inflammatory and antiallergic compounds of the glucocorticosteroids.

Surprisingly, it has been found that the compounds of the present invention show improved pharmacokinetic or pharmacodynamic characteristics, such as systemic exposure, selectivity and duration of action.

DETAILED DESCRIPTION OF THE PREFERRED EMBODIMENTS

In particular, the invention is directed to compounds of general formula (I):

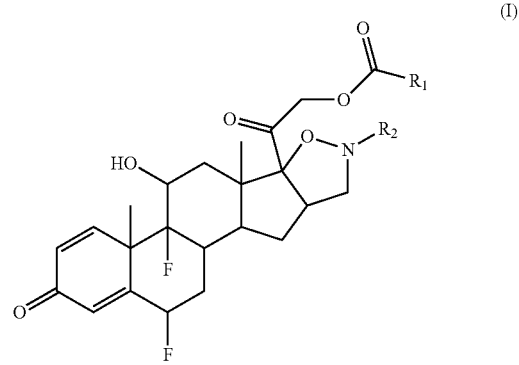

wherein

R$_1$ is linear or branched (C$_1$-C$_{16}$)alkyl, linear or branched (C$_2$-C$_{18}$)alkenyl, —OR$_6$, aryl, aryl(C$_1$-C$_{16}$)alkyl, —SR$_6$, —N(R$_4$)(R$_5$), (C$_3$-C$_8$)cycloalkyl, (C$_3$-C$_8$)heterocycloalkyl, or heteroaryl, wherein optionally one or more hydrogen atoms are replaced by (C$_1$-C$_6$)alkyl, and wherein R$_4$ and R$_5$ are independently H or linear or branched (C$_1$-C$_6$)alkyl, and R$_6$ is linear or branched (C$_1$-C$_{16}$)alkyl;

R$_2$ is aryl optionally substituted by one or more halogen atoms; and pharmaceutically acceptable salts thereof.

In the present description, unless otherwise provided, the term "halogen" includes fluorine, chlorine, bromine and iodine atoms.

The term "(C$_1$-C$_{16}$)alkyl" refers to linear or branched chain alkyl groups wherein the number of carbon atoms is from 1 to 16. Examples of said groups are methyl, ethyl, n-propyl, isopropyl, n-butyl, isobutyl, sec-butyl, tert-butyl, pentyl, hexyl, heptyl, octyl, ethyl-butyl, propyl-butyl, methyl-butyl, ethyl-methyl-propyl, hexadecyl, undecyl, dodecyl, tridecyl, quaterdecyl, quindecyl, hexadecyl, and the like.

The expression "(C$_2$-C$_{18}$)alkenyl" refers to linear or branched carbon chains with one or more double bonds, wherein the number of carbon atoms is from 2 to 18. Examples of said groups include ethenyl, propenyl, butenyl, pentenyl, hexenyl, heptenyl, octenyl, nonenyl, decenyl, undecenyl, dodecenyl, tridecenyl, quaterdecenyl, quindecenyl, hexadecenyl, heptadecenyl, and the like.

The expression "(C$_3$-C$_8$)cycloalkyl" refers to mono- or bi-cycloaliphatic hydrocarbon groups with from 3 to 8 carbon atoms. Examples include cyclopropyl, cyclobutyl, cyclopentyl, cyclohexyl, cycloheptyl, bicyclo[2.2.1]hept-2-yl, and the like.

The expression "(C$_3$-C$_8$)heterocycloalkyl" refers to (C$_3$-C$_8$)cycloalkyl groups, in which at least one ring carbon atom is replaced by a heteroatom or heteroaromatic group (e.g. N, NH, S or O). Examples include piperazinyl, thiazolidinyl, pyrrolidinyl, piperidinyl, morpholinyl, and the like.

The expression "aryl" refers to mono-, bi- or tri-cyclic ring systems which have 6 to 20 ring atoms, preferably from 6 to 15 and wherein at least one ring is aromatic. Examples of suitable aryl monocyclic systems include benzene radical (phenyl) and the like. Examples of suitable aryl bicyclic systems include naphthalene (naphthyl), biphenylene (biphenylenyl) radicals and the like. Examples of suitable aryl tricyclic systems include fluorine radical (fluorinyl) and the like.

The expression "aryl(C$_1$-C$_6$)alkyl" refers to (C$_1$-C$_6$)alkyl groups further substituted by aryl.

As used herein, the term "heteroaryl" refers to mono-, bi- or tricyclic ring system which have 5 to 20 ring atoms, preferably from 5 to 15, in which at least one ring is aromatic and in which at least one ring atom is a heteroatom or heteroaromatic group (e.g. N, NH, S or O).

Examples of suitable heteroaryl monocyclic systems include thiophene (thiophenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), piperidine (piperidinyl), piperazine (piperazinyl), and furan (furanyl) radicals such as tetrahydrofuran (tetrahydrofuranyl) and the like.

Examples of suitable heteroaryl bicyclic systems include purine (purinyl), pteridine (pteridinyl), benzotriazole (benzotriazolyl), quinolone (quinolinyl), isoquinoline (isoquinolinyl), indole (indolyl), isoindole (isoindolyl), benzofuran (benzofuranyl), benzodioxane (benzodioxaneyl), benzothiophene (benzothiphenyl) radicals and the like.

It will be apparent to those skilled in the art that compounds of general formula (I) contain asymmetric centers at least at the positions 4a, 4b, 5, 6a, 6b, 9a, 10a, 10b and therefore may exist as many optical stereoisomers and mixtures thereof. Therefore the invention is also directed to all of these forms and mixtures thereof.

Preferred compounds are those of general formula (I) wherein the stereochemistry of stereogenic carbon atoms is as reported in formula (I') below, in which the absolute configuration is assigned on the basis of Cahn-Ingold-Prelog nomenclature based on groups' priorities

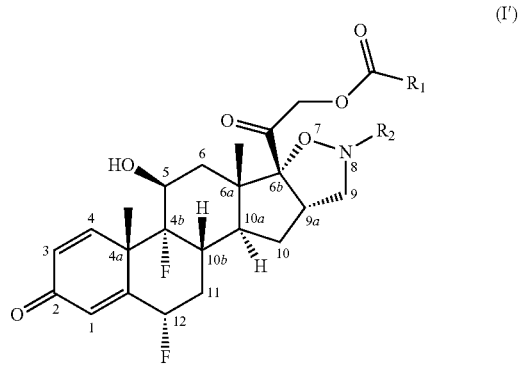

(I')

and wherein the meanings of R$_1$ and R$_2$ are as defined above.

In one preferred embodiment, for compounds of formula (I'), the absolute configuration at asymmetric center 4a is (S), at 4b is (R), at 5 is (S), at 6a is (S), at 6b is (R), at 9a is (S), at 10a is (S), at 10b is (S) and at 12 is (S).

Compounds of general formula (I) may form acid addition salts, particularly with pharmaceutically acceptable acids. Pharmaceutically acceptable acid addition salts of the compounds of formula (I), thus encompassing also those of formula (I'), include salts with inorganic acids, for example hydrohalogen acids such as hydrofluoric, hydrochloric, hydrobromic or hydroiodic; nitric, sulfuric, phosphoric; and organic acids, for example aliphatic monocarboxylic acids such as formic, acetic, trifluoroacetic and propionic; aliphatic hydroxyl acids such as lactic, citric, tartaric or malic; dicarboxylic acids such as maleic, fumaric, oxalic or succinic; aromatic carboxylic acids such as benzoic; aromatic hydroxy acids and sulfonic acids. These salts may be prepared from compounds of formula (I) or (I') by known salt-forming procedures.

It is to be understood that all preferred groups or embodiments described herebelow for compounds of formula (I) may be combined among each other and apply as well mutatis mutandis.

A preferred group of compounds of general formula (I) or (I') is that wherein R$_1$ is linear or branched (C$_1$-C$_{16}$)alkyl, linear or branched (C$_2$-C$_{18}$)alkenyl, —OR$_6$, aryl, aryl(C$_1$-C$_{16}$)alkyl, —SR$_6$, —N(R$_4$)(R$_5$), (C$_3$-C$_8$)cycloalkyl, (C$_3$-C$_8$)heterocycloalkyl, or heteroaryl, wherein optionally one or more hydrogen atoms are replaced by (C$_1$-C$_6$)alkyl and wherein R$_4$ and R$_5$ are independently H or linear or branched (C$_1$-C$_6$)alkyl and R$_6$ is linear or branched (C$_1$-C$_{16}$)alkyl; and R$_2$ is aryl optionally substituted by one or more halogen atoms.

Even more preferred within this group are the compounds of general formula (I) or (I') wherein $R_1$ is selected from the group consisting of methyl, isopropyl, ethyl, quindecyl, butyl, hexyl, heptadecenyl, methoxy, methylsulfanyl, isobutyl, isopentyl, tertbutyl, methylamino, dimethylamino, phenyl, cyclopropyl, cyclopentyl, methylpropanoxy, benzyl, piridyl, piperazinyl, piperidinyl, pyrrolidinyl, thiazolidinyl, and furyl; and $R_2$ is p-chlorophenyl.

Hereinafter, compounds of formula (I) and (I') and their pharmaceutically acceptable salts and solvates are referred to as "compounds of the present invention".

Examples of preferred compounds of the invention are:

| Compound | Chemical Name |
|---|---|
| 1 | Isobutyric acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 3 | Propionic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 4 | Hexadecanoic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 5 | Octadec-9-enoic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 6 | Pentanoic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 7 | Acetic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 8 | Benzoic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 9 | Methyl carbonate (Methyl formate) 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester) |
| 10 | S-methyl carbonothioate (or S-methyl methanethioate) 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 11 | 3-Methylbutanoic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 12 | Pivalic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 13 | 2-Phenylacetic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 14 | Furan-2-carboxylic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 15 | Cyclopentane-carboxylic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 16 | Cyclopropane-carboxylic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 17 | Isonicotinic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 18 | Isobutyl methyl carbonate 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo- |

| Compound | Chemical Name |
|---|---|
| | 2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 19 | Hexyl carbonate 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester) |
| 20 | Dimethyl 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl carbamate |
| 21 | Methyl 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl carbamate |
| 22 | Piperazine-1-carboxylic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 23 | Thiazolidine-4-carboxylic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 24 | Proline, 2-[(4aS,4bR,5S,6aS,6bR,9aS,10aS,10bS,12S)-8-(4-chloro-phenyl)-4b,12-difluoro-5-hydroxy-4$^a$,6$^a$-dimethyl-2-oxo-2,4a,4b,5,6,6$^a$,8,9,9$^a$,10,10$^a$,10b,11,12-tetradecahydro-7-oxa-8-aza-pentaleno[2,1-a]phenanthren-6b-yl]-2-oxo-ethyl ester |
| 25 | Piperidine-4-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |

According to analogous procedures and methods herein described, the preferred compounds of the invention from the list below reported, may be obtained:

| Compound | Chemical Name |
|---|---|
| 26 | Butanoic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 27 | Butanoic acid, 2-methyl-, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 28 | Cyclobutanecarboxylic acid, 2-[(4aS,4bR,5S,6aS,6bR,9aS,10aS,10bS,12S)-8-(4-chloro-phenyl)-4b,12-difluoro-5-hydroxy-4$^a$,6$^a$-dimethyl-2-oxo-2,4$^a$,4b,5,6,6$^a$,8,9,9$^a$,10,10$^a$,10b,11,12-tetradecahydro-7-oxa-8-aza-pentaleno[2,1-a]phenanthren-6b-yl]-2-oxo-ethyl ester |
| 29 | Cyclohexanecarboxylic acid, 2-[(4aS,4bR,5S,6aS,6bR,9aS,10aS,10bS,12S)-8-(4-chloro-phenyl)-4b,12-difluoro-5-hydroxy-4$^a$,6$^a$-dimethyl-2-oxo-2,4$^a$,4b,5,6,6$^a$,8,9,9$^a$,10,10$^a$,10b,11,12-tetradecahydro-7-oxa-8-aza-pentaleno[2,1-a]phenanthren-6b-yl]-2-oxo-ethyl ester |
| 30 | 2-Thiophenecarboxylic acid, tetrahydro-, 2-[(4aS,4bR,5S,6aS,6bR,9aS,10aS,10bS,12S)-8-(4-chloro-phenyl)-4b,12-difluoro-5-hydroxy-4$^a$,6$^a$-dimethyl-2-oxo-2,4$^a$,4b,5,6,6$^a$,8,9,9$^a$,10,10$^a$,10b,11,12-tetradecahydro-7-oxa-8-aza-pentaleno[2,1-a]phenanthren-6b-yl]-2-oxo-ethyl ester |
| 31 | 2H-thiopyran-4-carboxylic acid, tetrahydro-, 2-[(4aS,4bR,5S,6aS,6bR,9aS,10aS,10bS,12S)-8-(4-chloro-phenyl)-4b,12-difluoro-5-hydroxy-4$^a$,6$^a$-dimethyl-2-oxo-2,4$^a$,4b,5,6,6$^a$,8,9,9$^a$,10,10$^a$,10b,11,12-tetradecahydro-7-oxa-8-aza-pentaleno[2,1-a]phenanthren-6b-yl]-2-oxo-ethyl ester |
| 32 | Cyclopentanecarboxylic acid, 2,5-dimethyl-, 2-[(4aS,4bR,5S,6aS,6bR,9aS,10aS,10bS,12S)-8-(4-chloro-phenyl)-4b,12-difluoro-5-hydroxy-4$^a$,6$^a$-dimethyl-2-oxo-2,4$^a$,4b,5,6,6$^a$,8,9,9$^a$,10,10$^a$,10b,11,12-tetradecahydro-7-oxa-8-aza-pentaleno[2,1-a]phenanthren-6b-yl]-2-oxo-ethyl ester |

| Compound | Chemical Name |
| --- | --- |
| 33 | Cyclohexanecarboxylic acid, 2,6-dimethyl-, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 34 | 3-Pyridinecarboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 35 | 1H-pyrrole-3-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 36 | 3-Thiophenecarboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 37 | 3-Furancarboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 38 | 1H-indole-7-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 39 | 1H-Indene-7-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 40 | 8-Quinolinecarboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 41 | Quinoline-3-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 42 | Benzo[b]thiophene-3-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 43 | 1H-Indole-3-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 44 | Benzofuran-3-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 45 | Benzofuran-2-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 46 | 2-Thiophenecarboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 47 | 2-Furancarboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |

| Compound | Chemical Name |
|---|---|
| 48 | 1H-Pyrrole-2-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 49 | Tetrahydro-2H-pyran-4-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 50 | 4-Methylpiperazine-1-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 51 | Morpholine-4-carboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 52 | 2-Pyridinecarboxylic acid, 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |

The present invention also provides pharmaceutical compositions comprising a compound of the present invention, either as such or as pharmaceutically acceptable salt, and one or more pharmaceutically acceptable carriers and/or excipients.

The compounds of the present invention may be administered as the sole active agent or in combination with one or more other pharmaceutical active ingredients including those currently used in the treatment of respiratory disorders, e.g. beta2-agonists, antimuscarinic agents, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), antitussive agents, mucus regulators, mucolytics, expectorant/mucokinetic modulators, peptide mucolytics, antibiotics, inhibitors of JAK, SYK inhibitors, inhibitors of PI3Kdelta or PI3Kgamma, M3-antagonists/beta2-agonists (MABA), and M3-antagonists/PDE4-inhibitors (MAPI).

The present invention also provides combinations of a compound of the present invention, either as such or as pharmaceutically acceptable salt, with a β2-agonist selected from the group consisting of carmoterol, GSK-642444, indacaterol, milveterol, arformoterol, arformoterol tartrate, formoterol, formoterol fumarate, salmeterol, salmeterol xinafoate, salbutamol, albuterol, levalbuterol, terbutaline, indacaterol (QAB-149), AZD-3199, BI-1744-CL, LAS-100977, GSK159797, GSK59790, GSK159802, GSK642444, GSK678007, GSK96108, bambuterol, isoproterenol, procaterol, clenbuterol, reproterol, fenoterol, bitolterol, brodxatelor and ASF-1020 and salts thereof.

The present invention also provides combinations of a compound of the present invention, either as such or as pharmaceutically acceptable salt, with an antimuscarinic agent selected from the group consisting of aclidinium, tiotropium, tiotropium bromide (Spiriva®), ipratropium, ipratropium bromide, trospium, glycopyrrolate, NVA237, LAS34273, GSK656398, GSK233705, GSK57319, LAS35201, QAT370, and oxitropium salts.

The present invention also provides combinations of a compound of the present invention, either as such or as pharmaceutically acceptable salt, with a PDE4 inhibitor selected from the group consisting of AN-2728, AN-2898, CBS-3595, apremilast, ELB-353, KF-66490, K-34, LAS-37779, IBFB-211913, AWD-12-281, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the present invention, either as such or as pharmaceutically acceptable salt, with a P38 MAP kinase inhibitor selected from the group consisting of semapimod, talmapimod, pirfenidone, PH-797804, GSK-725, GSK856553, GSK681323, minokine, and losmapimod and salts thereof.

In a preferred embodiment, the present invention provides combinations of a compound of the invention with an IKK2 inhibitor.

The present invention also provides combinations of a compound of the present invention with a FINE inhibitor selected from the group consisting of AAT, ADC-7828, aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The present invention also provides combinations of a compound of the present invention with a leukotriene modulator selected from the group consisting of montelukast, zafirlukast, and pranlukast.

The present invention also provides combinations of a compound of the present invention with a NSAID selected from the group consisting of ibuprofen and ketoprofen.

The present invention also provides combinations of a compound of the present invention with an antitussive agent, selected from the group consisting of codeine and dextramorphan.

The present invention also provides combinations of a compound of the present invention with a mucolytic, selected from the group consisting of N acetyl cysteine and fudostein.

The present invention also provides combinations of a compound of the present invention with an expectorant/mucokinetic modulator, selected from the group consisting of ambroxol, hypertonic solutions (e.g. saline or mannitol) and surfactant. The present invention also provides combinations of a compound of the present invention with a peptide mucolytic, selected from the group consisting of recombinant human deoxyribonuclease I (dornase-alfa and rhDNase) and helicidin.

The present invention also provides combinations of a compound of the present invention, with an antibiotic, selected from the group consisting of azithromycin, tobramycin, and aztreonam.

The present invention also provides combinations of a compound of the present invention with a mucus regulator selected from the group consisting of INS-37217, diquafosol, sibenadet, CS-003, talnetant, DNK-333, MSI-1956, and gefitinib.

The present invention also provides combinations of a compound of the present invention, either as such or as pharmaceutically acceptable salt, with an inhibitor of JAK, selected from the group consisting of CP-690550 and GLPG0634.

The present invention also provides combinations of a compound of the present invention, either as such or as pharmaceutically acceptable salt, with a SYK inhibitor selected from the group consisting of R406, R343, and PRT062607.

The present invention also provides a compound of the present invention for use as a medicament.

The present invention also relates to the use of a compound of the present invention to decrease the number, activity and movement of the inflammatory cells in vitro and/or in vivo.

The present invention is also directed to compounds of the present invention for use in the prevention or treatment of any disease wherein the decrease in the number, activity and movement of inflammatory cells is involved.

In a further aspect, the present invention provides the use of compounds of the present invention for the prevention and/or treatment of any disease wherein the decrease in the number, activity and movement of inflammatory cells is involved.

In particular, compounds of the present invention, either alone or combined with one or more active ingredients, may be administered for the prevention and/or treatment of a disease of the respiratory tract characterized by airway obstruction such as asthma and COPD.

In a further aspect the present invention provides the use of compounds of the present invention for the preparation of a medicament for the prevention and/or treatment of any disease wherein the decrease in the number, activity and movement of inflammatory cells is involved.

Moreover the present invention provides a method for prevention and/or treatment of any disease wherein the decrease in the number, activity and movement of inflammatory cells is involved, said method comprising administering to a patient in need of such treatment a therapeutically effective amount of a compound of the invention.

The present invention also provides pharmaceutical preparations of compounds of the present invention suitable for administration by inhalation, by injection, orally or intra-nasally. Inhalable preparations include inhalable powders, propellant-containing metering aerosols, and propellant-free inhalable formulations.

The present invention is also directed to a device which may be a single- or multi-dose dry powder inhaler, a metered dose inhaler or a nebulizer, in particular a soft mist nebulizer containing a compound of the present invention.

The present invention is also directed to a kit comprising a pharmaceutical composition of a compound of the present invention alone or in combination with or in admixture with one or more pharmaceutically acceptable carriers and/or excipients and a device which may be a single- or multi-dose dry powder inhaler, a metered dose inhaler or a nebulizer.

The compounds of the present invention may be prepared according to a variety of synthetic steps which are carried out according to conventional methods and techniques or which are hereinbelow described.

In one aspect, the invention provides processes for the preparation of compounds of the present invention and intermediates thereof.

Some of the processes used for the preparation of the compounds of formula (I'), as described in the Scheme below, may also be applied to compounds of formula (I).

Scheme

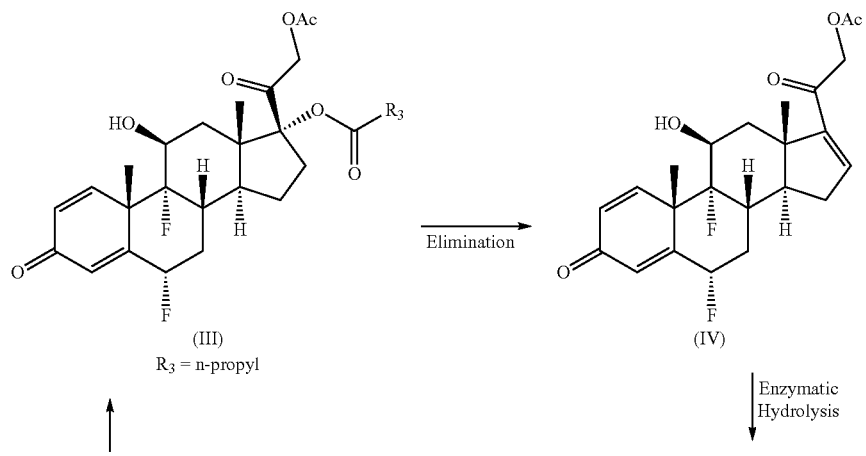

(III)
$R_3$ = n-propyl (IV)

Elimination

Enzymatic Hydrolysis

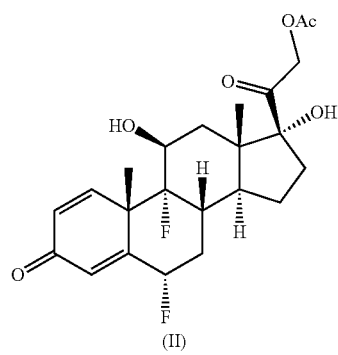

(II)

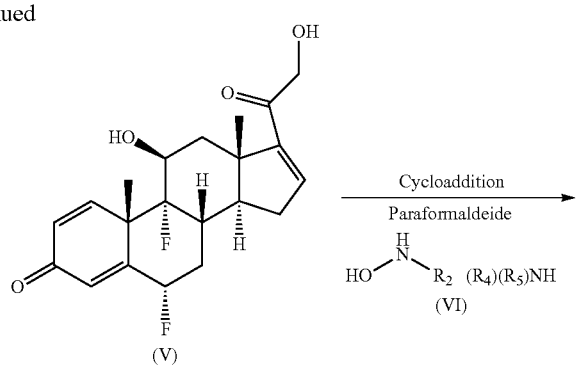

(V)

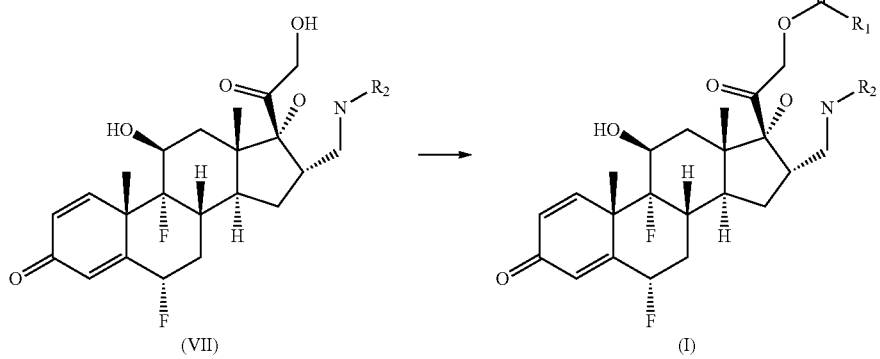

Procedures for the Preparation of the Compounds of the Present Invention.

According to particular embodiments, the compounds of the invention may be prepared according to different routes described in the above scheme, depending on the nature of the substituents $R_1$ and $R_2$.

In general, the compounds of the present invention may be prepared by the methods illustrated in the general reaction scheme or by modification thereof, using readily available starting materials, reagents and conventional synthesis procedures. In these reactions, it is also possible to make use of variants that are well known to the person skilled in the art.

Compounds of formula (III) may be readily prepared from known compounds by known methods, starting from compounds of general formula (II) (see J. Med. Chem., 1982, 25, 1492-1495, which is incorporated herein by reference in its entirety). They are also commercially available.

The compounds of formula (IV) may be conveniently prepared according to standard procedures reported in the literature. For instance they may be prepared by treatment of compounds of general formula (III) with a base such as potassium acetate. This reaction is usually performed in a suitable polar solvent such as DMF and typically proceeds at a temperature range from 80 to 110° C., over a period of 0.5 to 4 hours.

The compounds of formula (V) may be prepared by hydrolyzing the compounds of formula (IV). This reaction is preferably carried out by subjecting compounds (IV) to the action of an enzyme, such as immobilized Lipase from *Candida antarctica* (Sigma Aldrich) (see Tetrahedron, 50, 13165-13172, 1994, which is incorporated herein by reference in its entirety).

The compounds of general formula (VII) may be prepared starting from the reaction of a compound of formula (V) with a compound of formula (VI) in the presence of paraformaldehyde, using known procedures for the isoxazolidine formation, by cycloaddition of nitrones (see *J. Med. Chem.*, 25, 1492-1495, 1982, which is incorporated herein by reference in its entirety). The reaction is conveniently carried out in a protogenic solvent, such as ethanol, at temperatures ranging from 80 to 100° C. Hydroxyl amines of formula (VI) are either commercially available or may be easily prepared using known procedures, for example by reducing an oxime with a reducing agent, such as borane pyridine complex (see *J. Med. Chem.*, 40, 1955-1968, 1997, which is incorporated herein by reference in its entirety) or by reaction of O-tetrahydropyranyl hydroxylamine with a suitable alkylating agent such as alkyl halides (see *Chem. Pharm. Bull.*, 46, 966-972, 1998, which is incorporated herein by reference in its entirety).

Conversion of the hydroxyl group of compounds of general formula (VII) into an ester, carbonate, carbamate or thiocarbonate, may be easily performed by reacting compounds of general formula (VII) with compounds of general formula (VIII), (IX), (X), (XI), (XII) or (XIII) following the described synthetic route (Routes A through D).

The skilled person may introduce, where appropriate, suitable variations to the conditions specifically described in the examples in order to adapt the synthetic routes to the provision of further compounds of the invention. Such variations may include, but are not limited to, use of appropriate starting materials to generate different compounds, changes in the solvent and temperature of reactions, replacements of a reactant with analogous chemical role, introduction or removal of protection/deprotection stages of functional groups sensitive to reaction conditions and reagents, as well as introduction or removal of specific synthetic steps oriented to further fictionalization of the chemical scaffold.

Reaction of the intermediates of general formula (VII) with acyl chlorides (VIII), following Route A, to obtain compounds of general formula (I) is conveniently performed in DCM (dichloromethane) as solvent in the presence of a base such as triethylamine, DIPEA (N,N-diisopropyl-ethylamine) or pyridine at RT over a period of 4 to 50 hours.

Alternatively, with Route B, conversion of the hydroxyl group of compounds of general formula (VII) into a carbamate may be easily performed by reacting compounds of general formula (VII) with compounds of general formula (IX), following known procedures. The reaction is conveniently performed in DCM as solvent in the presence of a base such as DMAP, at RT over a period of 4 to 50 hours.

Following using Route C, reaction of the intermediates of general formula (VII) with CDI (1,1'-Carbonyldiimidazole) followed by addition of desired alcohol (X) or thiol (XI) or amine (XII) to obtain compounds of general formula (I) is conveniently performed in THF (tetrahydrofuran) at RT over a period of 4 to 50 hours.

Alternatively, according to Route D, conversion of the hydroxyl group of compounds of general formula (VII) into compounds of general formula (I) can be achieved by reacting compounds of general formula (XIII) with HOBt (hydroxybenzotriazole) followed by adding of compounds of general formula (VII), EDC (1-ethyl-3-(3-dimethylaminopropyl)carbodiimide) and DMAP (4-dimethylaminopyridine). The reaction is conveniently performed in DMF as solvent at RT over a period of 4 to 50 hours.

From all of the above, it should be clear to the skilled person that any of the described groups may be present as such or in any properly protected form. In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates the protective groups which were adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, 20 T.W. Green; Protective Groups in Organic Synthesis (Wiley, N.Y. 1981), which is incorporated herein by reference in its entirety).

From all of the above, it is clear to the person skilled in the art that by selecting the starting material with a proper stereochemical configuration, any of the possible stereoisomers of formula (I) can be obtained.

Advantageously, the compounds of the present invention may be administered for example, at a dosage of from 0.001 to 1000 mg/day, preferably from 0.1 to 500 mg/day.

When they are administered by the inhalation route, the dosage of the compounds of the present invention is advantageously from 0.01 to 20 mg/day, preferably from 0.1 to 10 mg/day.

Preferably, the compounds of the present invention alone or combined with one or more other active ingredients may be administered for the prevention and/or treatment of any obstructive respiratory disease such as asthma, chronic bronchitis, and chronic obstructive pulmonary disease (COPD).

However the compounds of the present invention may be administered for the prevention and/or treatment of any disease wherein the decrease in the number, activity and movement of inflammatory cells is involved.

Examples of such diseases include: diseases involving inflammation such as asthma and other allergic disorders, COPD, acute rhinitis; reverse acute transplant rejection and acute exacerbations of selected autoimmune disorders, graft-versus-host disease in bone-marrow transplantation; autoimmune disorders such as rheumatoid and other arthritis; skin conditions such as systemic lupus erythematosus, systemic dermatomyositis, psoriasis; inflammatory bowel disease, inflammatory ophthalmic diseases, autoimmune hematologic disorders, and acute exacerbations of multiple sclerosis; kidney, liver, heart, and other organ transplantation; Behçet's acute ocular syndrome, endogenous uveitis, atopic dermatitis, inflammatory bowel disease, and nephrotic syndrome; Hodgkin's disease and non-Hodgkin's lymphoma, multiple myeloma and chronic lymphocytic leukemia (CLL); autoimmune hemolytic anemia and thrombocytopenia associated with CLL, leukemia, and malignant lymphoma.

Preferably the compounds of the invention may be administered for the prevention and/or treatment of respiratory diseases such as from mild to acute severe conditions of asthma and COPD.

Other features of the invention will become apparent in the course of the following descriptions of exemplary embodiments which are given for illustration of the invention and are not intended to be limiting thereof.

EXAMPLES

In the reported experimental procedures, the following abbreviations may be used:
TEA=triethylamine;
DCM=dichloromethane;
RT=room temperature;
AcOEt=ethyl acetate;
DMF=N,N-dimethylformamide;
DMSO dimethylsulfoxide;
HATU=O-(7-azabenzotriazol-1-yl)-N,N,N',N'-tetramethyl-uronium hexafluorophosphate;
DMAP=4-dimethylaminopyridine; and
DIPEA32 ethyldiisopropylamine.

Example 1

Preparation of isobutyric acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester (Compound 1)

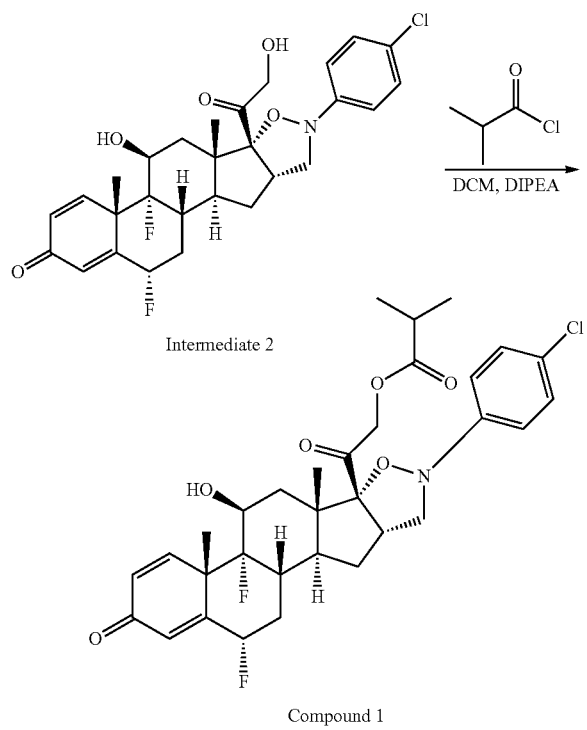

Intermediate 2

Compound 1

To a stirred solution of intermediate 2 (600 mg, 1.124 mmol) and DIPEA (0.391 ml, 2.247 mmol) in dry dichloromethane (30 ml), under nitrogen atmosphere at 5° C., isobutyryl chloride (0.235 ml, 2.247 mmol) was added, and the reaction mixture was stirred at 5° C. for 10 minutes and at RT for 16 hours. DIPEA (0.196 ml, 1.124 mmol) and isobutyryl chloride (0.118 ml, 1.124 mmol) were further added, and the mixture was stirred at RT for 72 hours. Another portion of DIPEA (0.196 ml, 1.124 mmol) and isobutyryl chloride (0.118 ml, 1.124 mmol) were further added, and the reaction mixture was stirred at RT for 1 hour and at 50° C. for 1.5 hours. The reaction mixture was diluted with DCM (100 ml), and the organic layer was washed with 1 N HCl, a saturated solution of $NaHCO_3$ and brine, dried ($Na_2SO_4$) and concentrated. The crude was purified by silica gel flash chromatography in gradient elution from DCM/AcOEt 98:2 to DCM/AcOEt 92:8, to afford 481 mg of pure compound (71% yield; Rf=0.37 in AcOEt/DCM 10:90).

$^1$H NMR (300 MHz, DMSO-$d_6$) ppm 7.31-7.45 (m, 2 H), 7.26 (dd, 1 H), 6.98-7.10 (m, 2 H), 6.29 (dd, 1 H), 6.08 (s, 1 H), 5.62 (d, 1 H), 5.42-5.78 (m, 1 H), 5.06 (d, 1 H), 4.90 (d, 1 H), 4.18-4.32 (m, 1 H), 4.17 (t, 1 H), 3.44-3.62 (m, 1 H), 2.56-2.71 (m, 2 H), 2.63 (spt, 1 H), 2.04-2.34 (m, 3 H), 1.84-1.96 (m, 1 H), 1.63-1.83 (m, 1 H), 1.52-1.63 (m, 2 H), 1.50 (s, 3 H), 1.14 (d, 3 H), 1.13 (d, 3 H), 0.94 (s, 3 H)

LC-MS (ESI POS): 604.10 MH+

$[\alpha]_D^{25}$=+58.3 (c 0.2; MeOH)

The compounds listed in Table were prepared as previously described for compound 1, by acylation of intermediate 2 with suitable acyl chlorides.

TABLE 1

| Compound | Structure | Yield | Analytical |
|---|---|---|---|
| 3 | 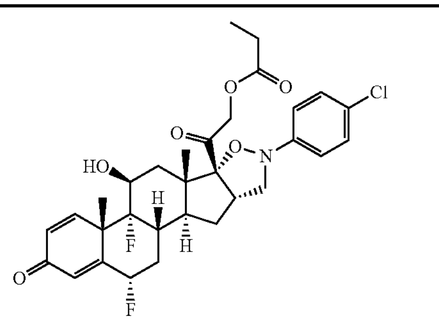 | 61% | LC-MS (ESI POS): 590.14 MH+<br>$[a]_D^{25}$ = + 59.7 (c 0.2 MeOH)<br>$^1$H NMR (300 MHz, DMSO-$d_6$)<br>ppm 7.31-7.43 (m, 2H), 7.26 (dd, 1H), 6.90-7.10 (m, 2H), 6.29 (dd, 1H), 6.08 (s, 1H), 5.62 (dd, 0H), 5.45-5.73 (m, 1H), 5.06 (d, 1H), 4.90 (d, 1H), 4.19-4.31 (m, 1H), 4.17 (t, 1H), 3.45-3.64 (m, 1H), 2.56-2.69 (m, 2H), 2.41 (q, 2H), 2.07-2.28 (m, 3H), 1.82-1.93 (m, 1H), 1.64-1.81 (m, 1H), 1.51-1.64 (m, 3H), 1.50 (s, 3H), 1.07 (t, 3H), 0.94 (s, 3H) |
| 4 | 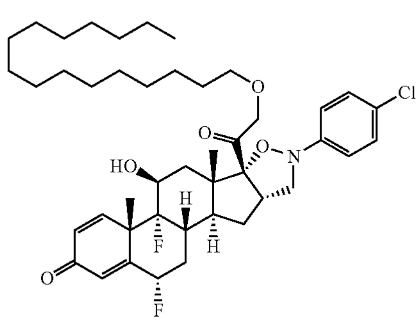 | 70% | LC-MS (ESI POS): 772.6 MH+<br>$[a]_D^{25}$ = + 65.9 (c 0.2 $CHCl_3$)<br>$^1$H NMR (300 MHz, DMSO-$d_6$) ppm 7.31-7.41 (m, 2H), 7.26 (d, 1H), 6.98-7.10 (m, 2H), 6.29 (dd, 1H), 6.08 (s, 1H), 5.62 (d, 1H), 5.43-5.79 (m, 1H), 5.06 (d, 1H), 4.89 (d, 1H), 4.18-4.29 (m, 1H), 4.17 (t, 1H), 3.45-3.61 (m, 1H), 2.55-2.73 (m, 2H), 2.37 (t, 2H), 2.03-2.31 (m, 3H), 1.88 (d, 1H), 1.62-1.81 (m, 1H), 1.51-1.62 (m, 4H), 1.50 (s, 3H), 1.24 (s, 24H), 0.93 (s, 3H), 0.86 (t, 3H) |

TABLE 1-continued

| Compound | Structure | Yield | Analytical |
|---|---|---|---|
| 5 | 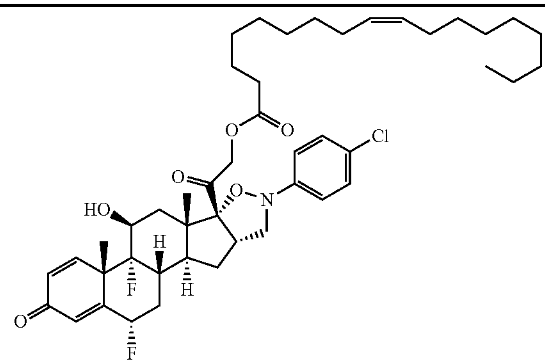 | | LC-MS (ESI POS): 798.31 MH+<br>$[a]_D^{25}$ = + 47 (c 0.0765; MeOH)<br>1H NMR (300 MHz, DMSO-d$_6$) ppm<br>7.30-7.39 (m, 2H), 7.26 (dd, 1H), 6.97-<br>7.09 (m, 2H), 6.29 (dd, 1H), 6.08 (s, 1H),<br>5.62 (d, 1H), 5.47-5.81 (m, 1H),<br>5.21-5.40 (m, 2H), 5.06 (d, 1H), 4.88<br>(d, 1H), 4.07-4.31 (m, 2H), 3.52 (q, 1H),<br>2.60 (dd, 2H), 2.37 (t, 2H), 2.06-2.26<br>(m, 3H), 1.92-2.05 (m, 4H), 1.87<br>(d, 1H), 1.62-1.80 (m, 1H), 1.50 (s, 3H),<br>1.45-1.61 (m, 4H), 1.26 (m, 20H),<br>0.93 (s, 3H), 0.85 (t, 3H) |
| 6 | 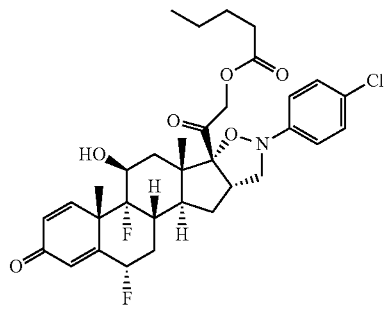 | 56% | LC-MS (ESI POS): 618.23 MH+<br>$[a]_D^{25}$ = + 68.6 (c 0.2 CHCl$_3$)<br>$^1$H NMR (300 MHz, DMSO-d$_6$) ppm<br>7.30-(m, 2H), 7.26 (dd, 1H), 6.93-<br>7.14 (m, 2H), 6.29 (dd, 1H), 6.08 (s, 1H),<br>5.62 (d, 1H), 5.42-5.79 (m, 1H),<br>5.07 (d, 1H), 4.89 (d, 1H), 4.23 (m, 1H),<br>4.17 (t, 1H), 3.43-3.63 (m, 1H),<br>2.55-2.66 (m, 2H), 2.39 (t, 2H),<br>2.00-2.25 (m, 3H), 1.88 (d, 1H), 1.63-1.81<br>(m, 1H), 1.42-1.61 (m, 4H), 1.50 (s, 3H),<br>1.26-1.41 (m, 2H), 0.93 (s, 3H),<br>0.81-0.92 (m, 3H) |
| 7 | 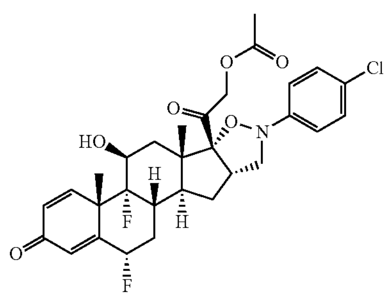 | 47% | LC-MS (ESI POS): 576.23 MH+<br>$[a]_D^{25}$ = + 53.8 (c 0.2 MeOH)<br>$^1$H NMR (300 MHz, DMSO-d$_6$) ppm<br>7.30-7.40 (m, 2H), 7.26 (dd, 1H), 6.88-<br>7.12 (m, 2H), 6.29 (dd, 1H), 6.08 (s, 1H),<br>5.62 (dd, 1H), 5.39-5.77 (m, 1H),<br>5.05 (d, 1H), 4.88 (d, 1H), 4.18-4.28<br>(m, 1H), 4.17 (t, 1H), 3.46-3.67 (m, 1H),<br>2.58-2.71 (m, 1H), 2.60 (dd, 1H),<br>2.12-2.32 (m, 3H), 2.10 (s, 3H), 1.81-<br>1.94 (m, 1H), 1.64-1.81 (m, 1H),<br>1.51-1.64 (m, 2H), 1.50 (s, 3H), 0.93 (s, 3H) |
| 8 | 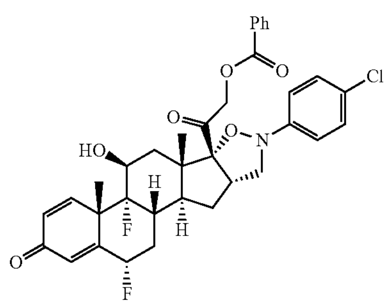 | 29% | LC-MS (ESI POS): 638.15 MH+<br>$[a]_D^{25}$ = + 66 (c 0.2 MeOH)<br>$^1$H NMR (300 MHz, DMSO-d$_6$) ppm<br>7.93-8.06 (m, 2H), 7.66-7.76 (m, 1H),<br>7.49-7.63 (m, 2H), 7.33-7.42 (m, 2H),<br>7.28 (dd, 1H), 7.00-7.15 (m, 2H),<br>6.30 (dd, 1H), 6.09 (s, 1H), 5.67 (dd, 1H),<br>5.49-5.85 (m, 1H), 5.35 (d, 1H),<br>(d, 1H), 4.23-4.32 (m, 1H), 4.21 (t, 1H),<br>3.47-3.65 (m, 1H), 2.56-<br>2.69 (m, 2H), 2.09-2.32 (m, 3H), 1.91-2.04<br>(m, 1H), 1.66-1.83 (m, 1H),<br>1.53-1.65 (m, 2H), 1.51 (s, 3H), 1.00 (s, 3H) |
| 9 | 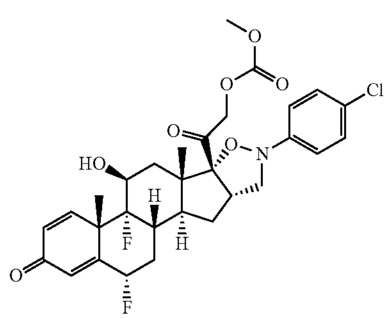 | 54% | LC-MS (ESI POS): 592.13 MH+<br>$[a]_D^{25}$ = + 48.6 (c 0.2 MeOH)<br>$^1$H NMR (300 MHz, DMSO-d$_6$) ppm<br>7.30-7.39 (m, 2H), 7.26 (dd, 1H), 6.96-<br>7.10 (m, 2H), 6.29 (dd, 1H), 6.08 (s, 1H),<br>5.63 (dd, 1H), 5.47-5.75 (m, 1H),<br>5.07 (d, 1H), 4.94 (d, 1H), 4.19-4.29 (m, 1H),<br>4.18 (t, 1H), 3.74 (s, 3H), 3.45-<br>3.61 (m, 1H), 2.62-2.72 (m, 1H), 2.61<br>(dd, 1H), 2.04-2.29 (m, 3H), 1.85 (d, 1H),<br>1.63-1.80 (m, 1H), 1.51-1.63 (m, 2H),<br>1.50 (s, 3H), 0.95 (s, 3H) |

TABLE 1-continued

| Compound | Structure | Yield | Analytical |
|---|---|---|---|
| 10 | 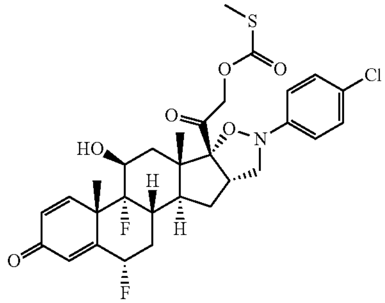 | 66% | LC-MS (ESI POS): 608.08 MH+<br>$[a]_D^{25}$ = + 50.8 (c 0.2 MeOH)<br>$^1$H NMR (300 MHz, DMSO-d$_6$) ppm 7.30-7.42 (m, 2H), 7.26 (d, 1H), 6.94-7.10 (m, 2H), 6.29 (dd, 1H), 6.08 (s, 1H), 5.63 (dd, 1H), 5.45-5.78 (m, 1H), 5.22 (d, 1H), 5.06 (d, 1H), 4.19-4.27 (m, 1H), 4.18 (m, 1H), 3.44-3.62 (m, 1H), 2.59-2.72 (m, 1H), 2.61 (dd, 1H), 2.34 (s, 3H), 2.02-2.29 (m, 3H), 1.80-1.89 (m, 1H), 1.64-1.79 (m, 1H), 1.51-1.62 (m, 2H), 1.50 (s, 3H), 0.94 (s, 3H) |
| 11 | 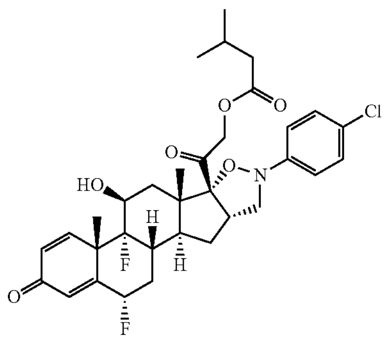 | 54% | LC-MS (ESI POS): 618.13 MH+<br>$[a]_D^{25}$ = + 63.4 (c 0.2 MeOH)<br>$^1$H NMR (300 MHz, DMSO-d$_6$) ppm 7.29-7.46 (m, 2H), 7.26 (dd, 1H), 6.94-7.13 (m, 2H), 6.29 (dd, 1H), 6.08 (s, 1H), 5.62 (dd, 1H), 5.39-5.81 (m, 1H), 5.08 (d, 1H), 4.89 (d, 1H), 4.21-4.39 (m, 1H), 4.17 (t, 1H), 3.41-3.63 (m, 1H), 2.56-2.70 (m, 2H), 2.27 (d, 2H), 2.07-2.25 (m, 3H), 1.94-2.09 (m, 1H), 1.80-1.94 (m, 1H), 1.64-1.80 (m, 1H), 1.51-1.62 (m, 2H), 1.50 (s, 3H), 0.94 (s, 3H), 0.95 (d, 6H) |
| 12 | 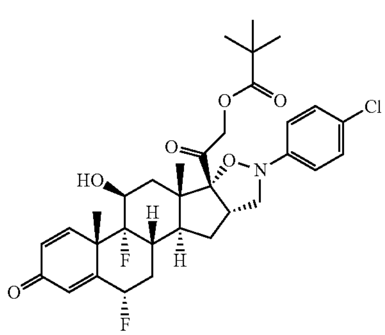 | 33% | LC-MS (ESI POS): 618.12 MH+<br>$[a]_D^{25}$ = + 53.6 (c 0.2 MeOH)<br>$^1$H NMR (300 MHz, DMSO-d$_6$) ppm 7.30-7.41 (m, 2H), 7.26 (dd, 1H), 6.95-7.12 (m, 2H), 6.29 (dd, 1H), 6.08 (s, 1H), 5.61 (d, 1H), 5.48-5.75 (m, 1H), 5.06 (d, 1H), 4.91 (d, 1H), 4.17 (t, 1H), 4.09-4.35 (m, 1H), 3.53 (q, 1H), 2.56-2.68 (m, 2H), 2.04-2.26 (m, 3H), 1.89 (d, 1H), 1.62-1.80 (m, 1H), 1.50 (s, 3H), 1.57 (d, 2H), 1.19 (s, 9H), 0.94 (s, 3H) |

TABLE 1-continued

| Compound | Structure | Yield | Analytical |
|---|---|---|---|
| 13 | 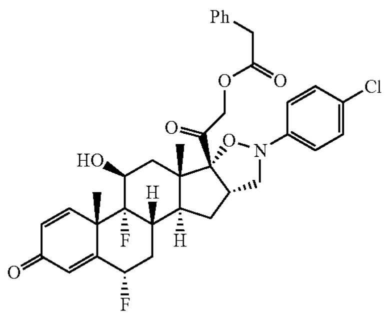 | 79% | LC-MS (ESI POS): 652.14 MH+<br>$[a]_D^{25} = +129.6$ (c 0.3; DCM)<br>1H NMR (300 MHz, DMSO-$d_6$) ppm<br>7.13-7.46 (m, 8H), 6.76-7.13 (m, 2H),<br>6.28 (dd, 1H), 6.08 (s, 1H), 5.60 (d, 1H),<br>5.40-5.77 (m, 1H), 5.10 (d, 1H),<br>4.93 (d, 1H), 4.11-4.31 (m, 2H), 3.78<br>(s, 2H), 3.43-3.66 (m, 1H), 2.55-<br>2.66 (m, 2H), 2.09-2.30 (m, 3H), 1.86<br>(d, 1H), 1.72 (d, 1H), 1.49 (s, 3H),<br>1.33-1.63 (m, 2H), 0.93 (s, 3H) |
| 14 | 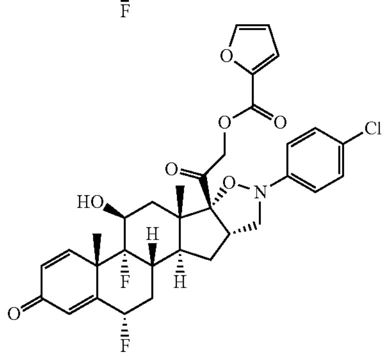 | 60% | LC-MS (ESI POS): 628.2 MH+<br>$[a]_D^{25} = +34.9$ (c 0.2, MeOH)<br>$^1$H NMR (300 MHz, DMSO-$d_6$) ppm<br>8.02 (dd, 1H), 7.32-7.43 (m, 3H), 7.27<br>(d, 1H), 6.98-7.13 (m, 2H), 6.73 (dd, 1H),<br>6.30 (dd, 1H), 6.09 (s, 1H), 5.66<br>(d, 1H), 5.46-5.79 (m, 1H), 5.30 (d, 1H),<br>5.11 (d, 1H), 4.20 (t, 1H), 4.09-<br>4.36 (m, 1H), 3.47-3.66 (m, 1H), 2.63<br>(dd, 2H), 2.06-2.27 (m, 3H), 1.93 (d,<br>1H), 1.64-1.83 (m, 1H), 1.56<br>(dd, 2H), 1.51 (s, 3H), 0.97 (s, 3H) |

Example 2

Preparation of Cyclopentanecarboxylic acid 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester (Compound 15)

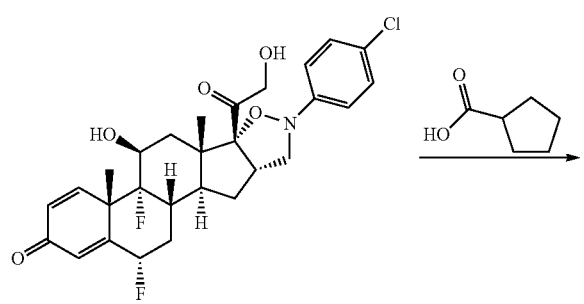

Intermediate 2

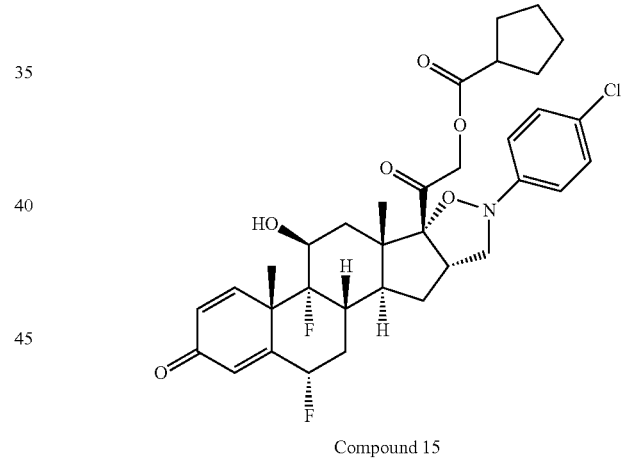

Compound 15

Cyclopentanecarboxylic acid (137 mg, 1.2 mmol, 1.2 eq) was dissolved in DMF (5 ml), 1-hydroxybenzotriazole hydrate (162 mg, 1.2 mmol, 1.2 eq) was added, and the reaction mixture was stirred 20 minutes. Intermediate 2 (534 mg, 1 mmol), 4-(dimethylamino)pyridine (305 mg, 2.5 mmol, 2.5 eq), and EDC*HCl (230 mg, 1.2 mmol, 1.2 eq) were added in this order, and the reaction mixture was stirred at RT overnight. The conversion was monitored by TLC analysis (Hex/EtOAc 7/6). The reaction was quenched with HCl 0.6N and the product extracted with EtOAc twice. The collected organic phases were washed with NaHCO$_3$ saturated solution, brine and dried over anhydrous Na$_2$SO$_4$. The crude was purified treating with NaOH 1N (10 ml), pyridine (used to transfer cylopentanecarboxylic acid in the aqueous layer, 2 ml), and EtOAc (30 ml). The organic layer was washed twice with water and filtered on a silica pad.

Compound 15 was obtained as a solid that was dried under vacuum at 50° C. for 2 hours (300 mg, yield 47.6%).

LC-MS (ESI POS): 630.10 MH+

$^1$H NMR (400 MHz, DMSO-$d_6$) δ ppm 7.34 (d, J=8.82 Hz, 2 H), 7.19-7.28 (m, 1 H), 7.04 (d, J=8.82 Hz, 2 H), 6.18-6.37 (m, 1 H), 5.97-6.13 (m, 1 H), 5.46-5.75 (m, 2 H), 4.78-5.17 (m, 2 H), 4.06-4.31 (m, 2 H), 3.42-3.55 (m, 1 H), 2.78-2.93 (m, 1 H), 2.54-2.74 (m, 2 H), 2.09 (m, 3 H), 1.49 (m, 15 H), 0.93 (s, 3 H).

The compounds listed in Table 2 were prepared as previously described.

TABLE 2

| Compound | Structure | Yield | Analytical |
|---|---|---|---|
| 16 | 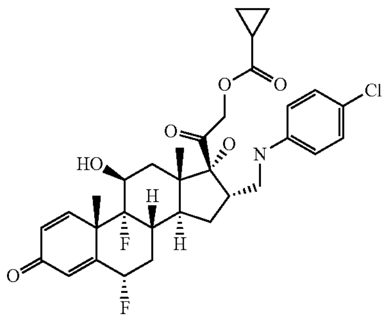 | 71% | LC-MS (ESI POS): 602.2 MH+<br>$^1$H NMR (400 MHz, DMSO-$d_6$) δ ppm 7.26-7.37 (m, 2H), 7.14-7.24 (m, 1H), 6.90-7.05 (m, 2H), 6.15-6.40 (m, 1H), 5.99-6.06 (m, 1H), 5.39-5.72 (m, 2H), 4.74-5.12 (m, 2H), 4.03-4.22 (m, 2H), 3.39-3.57 (m, 1H), 2.50-2.70 (m, 2H), 1.94-2.22 (m, 3H), 1.76-1.90 (m, 1H), 1.59-1.73 (m, 2H), 1.36-1.56 (m, 5H), 0.71-1.01 (m, 7H). |
| 17 | 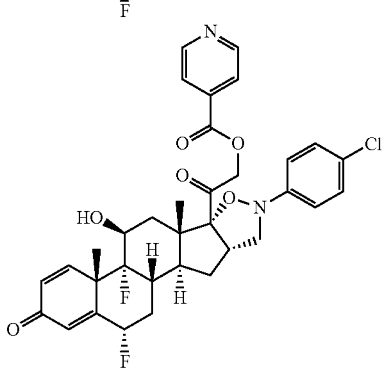 | 46% | LC-MS (ESI POS): 639.2 MH+<br>$^1$H NMR (400 MHz, DMSO-$d_6$) δ ppm 8.76-8.95 (m, 2H), 7.76-7.88 (m, 2H), 7.37 (d, J = 8.82 Hz, 2 H), 7.23-7.31 (m, 1H), 7.09 (d, J = 8.82 Hz, 2H), 6.24-6.35 (m, 1H), 6.09 (s, 1H), 5.51-5.76 (m, 2H), 5.11-5.45 (m, 2H), 4.09-4.32 (m, 2H), 3.48-3.65 (m, 1H), 2.59-2.75 (m, 2H), 2.12-2.36 (m, 3H), 1.89-2.06 (m, 1H), 1.51 (m, 6H), 0.98 (s, 3H). |

Example 3

Preparation of Isobutyl methyl carbonate 2-[(4aS, 4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester (Compound 18)

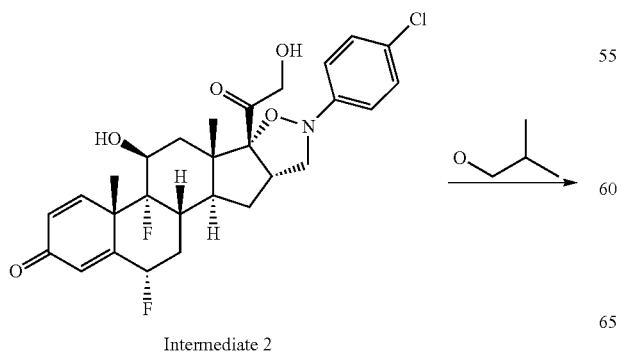

Intermediate 2

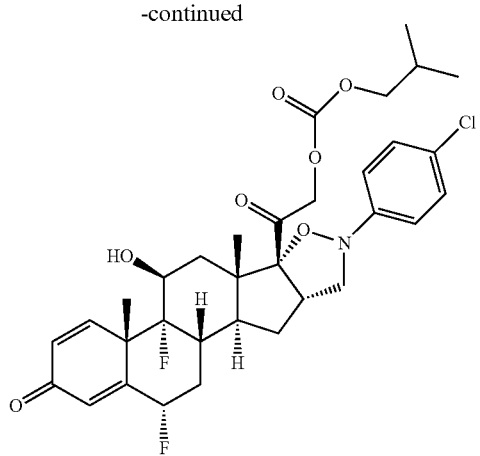

Compound 18

Intermediate 2 (350 mg, 0.66 mmol) in THF (3 ml) was added at RT with CDI (127 mg, 0.79 mmol, 1.2 eq) at portions. The reaction mixture was stirred 1 hour; conversion was detected by TLC analysis (EtOAc 100%). To the reaction mixture was added isobutyl alcohol (1.0 ml, 10 mmol) at 0° C. and stirred 1 hour at RT. Traces of the desired product were observed. The reaction mixture was then heated to 50° C. for four hours; conversion increase. After 12 hours at 50° C. complete conversion was detected by TLC analysis (hexane/EtOAc 3/7). The solvent was evaporated under vacuum and the crude treated with EtOAc/H$_2$O. The organic layers collected were dried over anhydrous Na$_2$SO$_4$, the crude was purified on a silica pad to yield compound 18 (240 mg, yield 58%).

LC-MS (ESI POS): 634.2 LC-MS
$^1$H NMR (400 MHz, DMSO-d$_6$) δ ppm 7.34 (d, J=8.82 Hz, 2 H), 7.20-7.30 (m, 1 H), 7.04 (d, J=8.82 Hz, 2 H), 6.21-6.37 (m, 1 H), 6.00-6.12 (m, 1 H), 5.47-5.72 (m, 2 H), 4.83-5.17 (m, 2 H), 4.10-4.29 (m, 2 H), 3.91 (dd, J=6.62, 0.88 Hz, 2 H), 3.43-3.60 (m, 1 H), 2.55-2.74 (m, 2 H), 2.04-2.29 (m, 3 H), 1.81-1.99 (m, 2 H), 1.64-1.76 (m, 1 H), 1.49 (m, 5 H), 0.81-0.96 (m, 9 H).

Compound 19 was prepared as previously described for compound 18 starting from hexyl alcohol.

| Compound | Structure | Yield | Analytical |
|---|---|---|---|
| 19 | 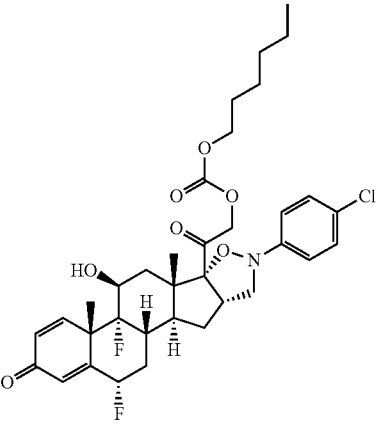 | 30% | LC-MS (ESI POS): 662.2 MH+ <br> $^1$H NMR (400 MHz, DMSO-d$_6$) δ ppm 7.33 (s, 2H), 7.18-7.29 (m, 1H), 7.00-7.11 (m, 2H), 6.22-6.37 (m, 1H), 6.02-6.11 (m, 1H), 5.49-5.77 (m, 2H), 4.79-5.17 (m, 2H), 4.14-4.27 (m, 2H), 4.04-4.13 (m, 2H), 3.44-3.62 (m, 1H), 2.53-2.68 (m, 2H), 2.03-2.29 (m, 3H), 1.77-1.90 (m, 1H), 1.49 (m, 8H), 1.22-1.36 (m, 6H), 0.76-0.99 (m, 6H). |

Example 4

Preparation of Dimethylcarbamate2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester (Compound 20)

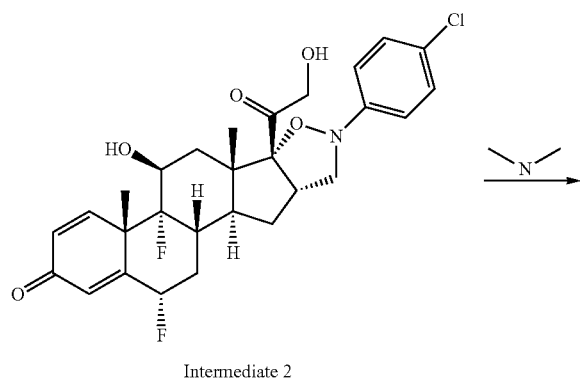

Intermediate 2

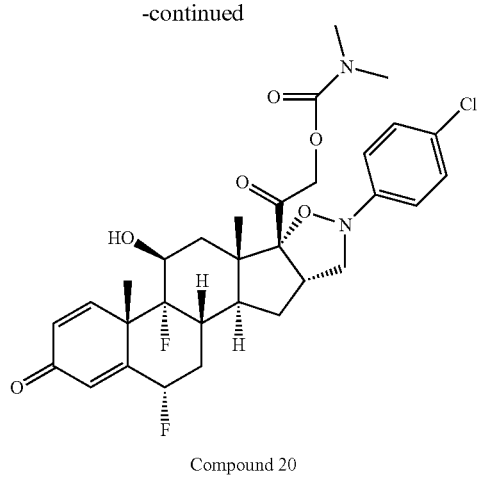

Compound 20

Intermediate 2 (310 mg, 0.58 mmol) in CH$_2$Cl$_2$ (3 ml) was added at RT with CDI (111 mg, 0.70 mmol, 1.2 eq) at portions. The reaction mixture was stirred 1 hour; complete conversion was detected by TLC analysis (EtOAc 100%). CH$_2$Cl$_2$ was evaporated under vacuum and the crude was dissolved in THF (2 ml) and then was added with 2 M dimethylamine solution in THF at 0° C. (1.15 ml, 2.32 mmol) and stirred 1 hour at RT. Complete conversion was detected by TLC analysis (hexane/EtOAc 2/8). The solvent was evaporated under vacuum and the crude treated with $CH_2Cl_2/H_2O$. The organic layers collected were dried over anhydrous $Na_2SO_4$, the crude was purified on a silica pad, then the obtained beige solid was triturated in a hexane/ethyl acetate mixture (8/2, 8 ml) for one night. The solid filtered was dried under vacuum at 50° C. till constant weight, yielding compound 20 (200 mg, yield 57%)

LC-MS (ESI POS): 605.2 LC-MS $^1$H NMR (400 MHz, DMSO-$d_6$) δppm 7.31-7.44 (m, 2 H), 7.21-7.30 (m, 1 H), 6.99-7.07 (m, 2 H), 6.20-6.43 (m, 1 H), 6.01-6.12 (m, 1 H), 5.47-5.76 (m, 2 H), 4.69-5.10 (m, 2 H), 4.08-4.25 (m, 2 H), 3.43-3.59 (m, 1 H), 2.80-3.00 (m, 6 H), 2.55-2.72 (m, 2 H), 2.03-2.28 (m, 3 H), 1.83-1.96 (m, 1 H), 1.65-1.81 (m, 1 H), 1.49 (m, 5 H), 0.93 (s, 3 H).

Compound 21 was prepared as previously described for compound 20 starting from methylamine.

| Compound | Structure | Yield | Analytical |
|---|---|---|---|
| 21 | 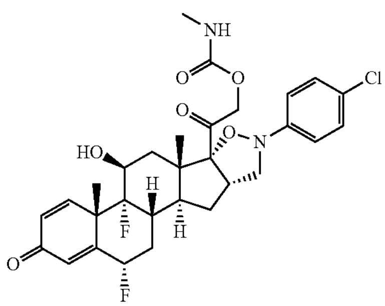 | 56.3% | LC-MS (ESI POS): 591.1 MR+ $^1$H NMR (400 MHz, DMSO-$d_6$) δ ppm 7.34 (d, J = 8.82 Hz, 2H), 7.15-7.28 (m, 2H), 7.03 (d, J = 8.82 Hz, 2H), 6.19-6.41 (m, 1H), 6.02-6.12 (m, 1H), 5.45-5.75 (m, 2H), 4.62-5.07 (m, 2H), 4.12-4.28 (m, 2H), 3.40-3.56 (m, 1H), 2.58 (m, 5H), 2.05-2.34 (m, 3H), 1.84-1.96 (m, 1H), 1.56-1.77 (m, 1H), 1.49 (s, 5H), 0.93 (s, 3H). |

Example 5

Preparation of Piperazine-1-carboxylic acid 2-[(4aS,4bR,5S,6aS,6bR,9aS,10aS,10bS,12S)-8-(4-chlorophenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester (Compound 22)

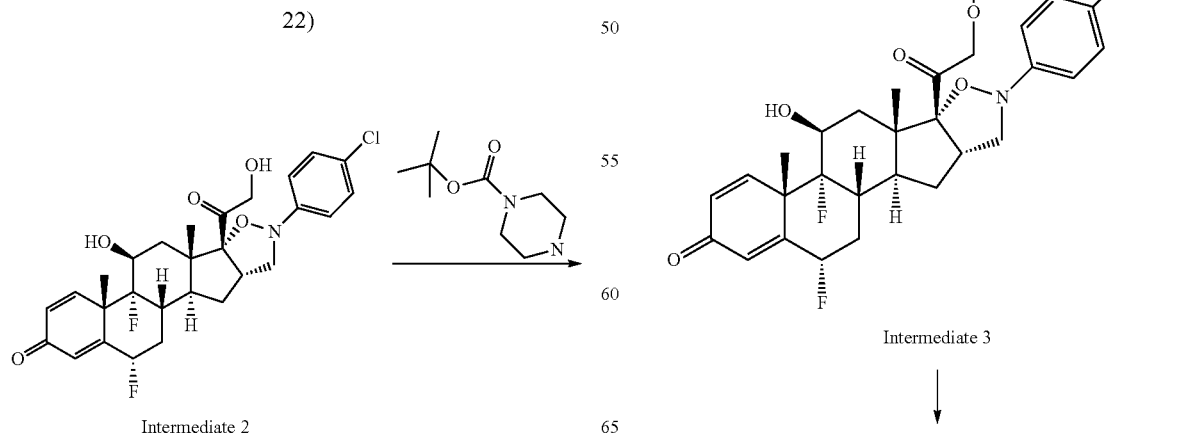

Intermediate 2

Intermediate 3

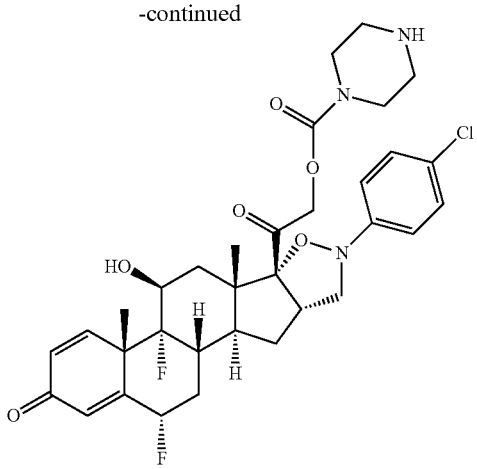

Compound 22

Intermediate 2 (500 mg, 0.94 mmol) in THF (3.5 ml) was added at RT with CDI (180 mg, 1.12 mmol, 1.2 eq) at portions. The reaction mixture was stirred 1 hour; complete conversion to activated intermediate was detected by TLC analysis (Hexane:EtOAc 3/7). The reaction mixture was cooled to 10° C. and then was added with tert-butyl piperazine-1-carboxylate (174 mg, 0.94 mmol, 1.0 eq) and stirred at RT overnight. Conversion was detected by TLC analysis (hexane/EtOAc 3/7). The solvent was evaporated under vacuum and the crude treated with EtOAc/$H_2O$. The organic layers collected were dried over anhydrous $Na_2SO_4$ and the crude compound intermediate 3 was used in the next step without further purification (260 mg, yield 37%). A solution of intermediate 3 (260 mg, 0.35 mmol) in $CH_2Cl_2$ (5 ml) was cooled to 0° C. and added dropwise with trimethyl-silyl trifluoromethanesulfonate (63 µl, 1.0 eq.). The reaction mixture was stirred 1 hour at 0° C. and then quenched with demineralised water. The organic layer was washed with $NaHCO_3$ saturated solution and then with demineralised water, dried over anhydrous $Na_2SO_4$ yielding raw compound, that was purified by column chromatography over silica gel (eluting with EtOAc/TEA 99:1) and dried under vacuum at 50° C. till constant weight to give compound compound 22 (190 mg, 84% yield)

LC-MS (EST POS): 646.4 MH+

$^1$H NMR (400 MHz, DMSO-$d_6$) δ ppm 7.33 (d, J=8.82 Hz, 3 H), 7.03 (d, J=8.82 Hz, 2 H), 6.19-6.39 (m, 1 H), 6.07 (s, 1 H), 5.46-5.76 (m, 2 H), 4.76-5.14 (m, 2 H), 4.05-4.28 (m, 2 H), 3.41-3.60 (m, 1 H), 3.18-3.30 (m, 5 H), 2.66 (m, 6 H), 1.95-2.28 (m, 3 H), 1.81-1.95 (m, 1 H), 1.57-1.79 (m, 1 H), 1.48 (m, 5 H), 0.93 (s, 3 H).

The compounds listed in the following Table were prepared as previously described for compound 22 starting from the corresponding intermediate.

| Compound | Structure | Yield | Analytical |
|---|---|---|---|
| 23 | 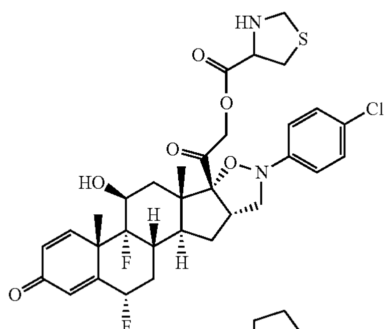 | 26% | LC-MS (ESI POS): 649.4 MH+<br>$^1$H NMR (400 MHz, DMSO-$d_6$) δ ppm 7.17-7.40 (m, 3H), 6.88-7.11 (m, 2H), 6.21-6.34 (m, 1H), 5.99-6.13 (m, 1H), 5.44-5.74 (m, 2H), 4.99-5.23 (m, 3H), 4.04-4.34 (m, 2H), 3.39-3.64 (m, 1H), 3.06-3.25 (m, 3H), 2.81-2.92 (m, 1H), 2.70-2.79 (m, 1H), 2.54-2.66 (m, 2H), 2.03-2.29 (m, 3H), 1.80-1.92 (m, 1H), 1.64-1.78 (m, 1H), 1.49 (m, 5 H), 0.93 (s, 3 H) |
| 24 | 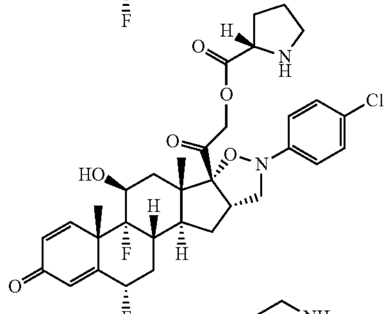 | 27% | LC-MS (ESI POS): 631.2 MH+<br>$^1$H NMR (400 MHz, DMSO-$d_6$) δ ppm 7.34 (m, 3H), 7.04 (d, J = 8.82 Hz, 2H), 6.22-6.41 (m, 1H), 6.08 (s, 1H), 5.41-5.78 (m, 2H), 4.74-5.18 (m, 2H), 4.08-4.26 (m, 2H), 3.69-3.84 (m, 1H), 3.42-3.59 (m, 1H), 2.71-2.96 (m, 2H), 2.54-2.69 (m, 2H), 1.96-2.25 (m, 5H), 1.80-1.93 (m, 2H), 1.60-1.75 (m, 3H), 1.49 (m, 5H), 0.93 (s, 3H) |
| 25 | 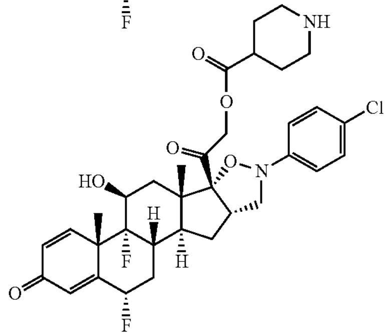 | 31% | LC-MS (ESI POS): 645.3 MH+<br>$^1$H NMR (400 MHz, DMSO-$d_6$) δ ppm 7.34 (d, J = 8.82 Hz, 3H), 7.04 (d, J = 8.82 Hz, 2H), 6.21-6.42 (m, 1H), 6.08 (s, 1H), 5.42-5.86 (m, 2H), 4.80-5.12 (m, 2H), 4.01-4.30 (m, 2H), 3.41-3.58 (m, 1H), 2.81-2.97 (m, 2H), 2.52-2.74 (m, 2H), 2.31-2.47 (m, 2H), 1.90-2.27 (m, 6H), 1.63-1.78 (m, 3H), 1.49 (m, 7H), 0.93 (s, 3H) |

Legend
* NMR
s=singlet
d=doublet
t=triplet
q=quartet
dd=doublet of doublets
m=multiplet
br=broad
ESI-POS=electrospray positive ionization
LC-MS=liquid chromatography-mass spectrometry
Pharmacological Activity of the Compounds of the Present Invention
In vivo Studies.

Example 6

Lipopolysaccharide (LPS)-induced Lung Neutrophilia

The potency and duration of action of the compounds described in the present invention were evaluated in vivo in an acute model of lung inflammation following a method described in *Am. J. Respir. Crit. Care Med.*, vol. 162, pp. 1455-1461 (2000), which is incorporated herein by reference in its entirety, with minor modifications. The tests were performed on Sprague-Dawley male rats (200 g). Intratracheal instillation of LPS resulted in a statistically significant increase in neutrophil concentration in BALF, a hallmark of acute ongoing pulmonary inflammation.

For the dose of glucocorticoid producing a 75% inhibition (ED75 dose) assessment test, compounds (0.01-1 μmoles/Kg of body weight) were administered intratracheally as suspension (0.2% Tween 80 in NaCl 0.9%) 1 hour before LPS challenge. A dose-response curve of the inhibitory effect of the test compounds on LPS-induced lung neutrophilia was performed and the ED50 dose of glucocorticoid was taken as a measure of potency in this bioassay. The ED50 dose values for some representative compounds of the present invention were comprised between 0.05 and 0.16 μmoles/Kg of body weight.

In a second series of experiments, aimed at the evaluation of the duration of action, the compounds were administered as suspension intratracheally, at the ED75 dose, administered 24 h before LPS challenge. The most interesting compounds were active (percent of inhibition higher than 50%) when administered 24 hours before LPS challenge.

In Vitro Studies

Example 7

Glucocorticoid Receptor (GR) Translocation Assay Protocol

A quantitative measurement of GR nuclear translocation of the compounds of the present invention was performed according to ASSAY Drug Devel. Technol., 4(3), pp. 263-272 (2006), which is incorporated herein by reference in its entirety, through a novel cell-based GR-translocation assay in Enzyme Fragment Complementation (EFC) format developed by DiscoveRx (Fremont, Calif.). In the absence of the glucocorticoid, the glucocorticoid receptor (GR) resides in the cytosol complexed with a variety of proteins including heat shock proteins. When a glucocorticoid diffuses through the cell membrane into the cytoplasm and binds to the glucocorticoid receptor (GR), it results in release of the heat shock proteins and the translocation into the nucleus where it modulates gene transcription.

The DiscoveRx assay uses EFC of b-galactosidase (b-gal) as an indicator of GR-translocation in engineered CHO-K1 biosensor cells. The enzyme acceptor (EA) fragment of b-gal resides in the nucleus, as designed through the use of a proprietary set of sequence additions and modifications. The small peptide enzyme donor (ED) fragment of b-gal was fused directly to the C-terminus of GR, and was localized in the cytoplasm in the absence of receptor signaling. Upon binding to a GR ligand, the complex translocates to the nucleus, where intact enzyme activity was restored by complementation and b-gal activity was detected.

CHO-K1 cells stably expressing NLS-enzyme acceptor fragment (EA) of b-gal and GR-enzyme donor (ED) fragment of b-gal were maintained in F12 medium (Invitrogen, Carlsbad, Calif.) at 37° C. under a humidified atmosphere containing 5% $CO_2$ and 95% air. The medium contained 10% FBS, 2 mM L-glutamine, 50 U/ml penicillin 50 μg/ml streptomycin, and 250 μg/ml hygromycin and 500 μg/ml G418 (Invitrogen). GR-translocation was measured using the PathHunter Detection Kit containing cell membrane permeabilizing reagent and beta-gal substrate (DiscoveRx, Fremont, Calif.). All compounds were screened using varying concentrations ranging from $10^{-11}$ to $10^{-6}$ M. The assay was performed in 48-wells (105 cells/well). Incubation with screened compounds was performed at 37° C. for two hours. Detection was made by adding the detection buffer from the kit supplied by DiscoveRx and incubating at RT for one hour. Luminescence was detected by using a CENTRO LB 960 microplate reader (Berthold Technologies). Statistical analysis and determinations of EC50s were performed by using Prism-version 3.0 Graphpad Software (San Diego, Calif.). Some representative compounds of the invention assayed with the GR translocation displayed a EC50 comprised between 3.2 nM and 207 nM.

Example 8

Inhibition of LPS-induced Nitric Oxide Production in RAW 264.7 Macrophages

An in vitro model based on macrophagic murine cell line RAW 264.7 was used for testing the anti-inflammatory effects of the corticosteroids of the present invention. During the inflammatory process, large amounts of nitric oxide (NO) were generated by the inducible isoforms of NO synthase (iNOS). Bacterial lipopolysaccharide (LPS) was commonly used in experimental settings to stimulate inflammatory responses in macrophages.

Cells were grown in a culture medium (RPMI supplemented with heat-inactivated 10% fetal calf serum, 2 mM glutamine, 100 U/ml penicillin and 0.1 mg/ml streptomycin) without phenol red. Cell stimulation was elicited by incubating cells for 24 hours with LPS to final concentrations ranging from 100 ng/ml. Treatments with the compounds of the invention were carried out by adding such compounds vehicled in DMSO (0.1% final concentration) to the final desired concentrations 15 minutes before LPS exposure. As an index of nitric oxide production, the concentration of nitrite was measured in the conditioned media by using the Griess colorimetric reaction (see *J. Neuroimmunol.*, vol. 150, pp. 29-36 (2004), which is incorporated herein by reference in its entirety).

Statistical analysis and determinations of IC50s were performed by using Prism-version 3.0 Graphpad Software (San Diego, Calif.). The IC50 values tested on some representative compounds of the invention were comprised between 12.2 and 151 nM.

Example 9

Interleukin-8 (IL-8) Release Assay Protocol

In order to evaluate the anti-inflammatory effects of novel inhaled corticosteroids, a selection of these compounds in inhibiting TNFα-induced IL-8 release from human airway smooth muscle cells (ASMCs) was assessed. hASMCs exposed to a variety of inflammatory mediators (Tumor Necrosis Factor (TNF)-α or IL-1β) can undergo phenotypic changes and secrete chemokines and cytokines, which may participate in or even perpetuate mucosal inflammatory changes via activation and recruitment of inflammatory cells (see Damera et al., 2009; Howarth et al., 2004; Chung, 2000; Koyama et al., 2000, all of which are incorporated herein by reference in their entireties).

Current evidence suggests that chemokines and cytokines secretion induced by inflammatory mediators is inhibited by glucocorticoids in hASMCs and lung fibroblasts (see John et al., 1998; Spoelstra et al., 2002; Tobler et al., 1992, all of which are incorporated herein by reference in their entireties). Steroids may inhibit the cytokine-induced secretion of chemokines by a direct inhibitory interaction between activated glucocorticoid receptors and activated transcription factors, such as nuclear factor-kappa B and activator protein-1 which modulated inflammatory gene expression. In addition, glucocorticoids can regulate chemokine expression by reducing mRNA stability through the rapid induction of potent endogenous inhibitor of p38 MAP Kinase, MKP-1, which is one of the genes trans-activated by steroids (see King et al., 2009, which is incorporated herein by reference in its entirety).

Primary human airway smooth muscle cells (ASMCs) were purchased from LONZA (Basel, CH) and cultured in DMEM medium supplemented with 10% Fetal Bovine Serum, 2 mM glutamine, 100 U penicillin and 100 µg/ml streptomycin (Invitrogen), in an atmosphere of 95% air and 5% $CO_2$ at 37° C. ASMCs were seeded in 0.5 ml DMEM containing 10% FBS in 48-well tissue culture plates at the density of 104 cells/well and grown for 24 hours at 37° C. with 5% $CO_2$. Then cells were serum starved for 18 hours before treatment with different concentration of LAGRA (10-12M-10-6M, final DMSO concentration 0.1%) for 60 min before stimulation with TNFα (0.1 ng/ml as final concentration for ASMCs). After 18 hours incubation in DMEM serum free, the IL8 release in the supernatant was assayed using ELISA kit (Invitrogen). Compound potencies were expresses as concentration able to inhibit the half maximal (50%) IL8 release [IC50] in the dose-response curve obtained after stimulation with TNFα.

All values stated are mean±standard error of mean (SEM). Compound potencies (expresses as half maximal (50%) inhibitory concentration [IC50]) were derived from a four-parameter non-linear iterative curve-fitting analysis using Prism software (Graph Pad Software, San Diego, Calif.). Statistical analysis, Sigmoid curves design and analysis were performed by using Prism software (Graph Pad Software, San Diego, Calif.).

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the treatment of asthma or Chronic Obstructive Pulmonary Disease (COPD), comprising administering to a subject in need thereof an effective amount of a compound of formula (I):

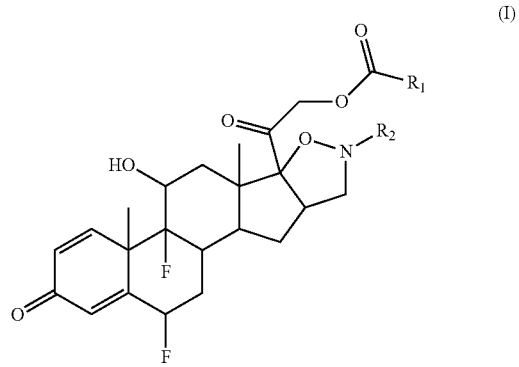

wherein
   $R_1$ is linear or branched $(C_1-C_{16})$alkyl, linear or branched $(C_2-C_{18})$alkenyl, —$OR_6$, aryl, aryl$(C_1-C_{16})$alkyl, —$SR_6$, —$N(R_4)(R_5)$, $(C_3-C_8)$cycloalkyl, $(C_3-C_8)$heterocycloalkyl, or heteroaryl, wherein optionally one or more hydrogen atoms are replaced by $(C_1-C_6)$alkyl, and wherein $R_4$ and $R_5$ are independently H or linear or branched $(C_1-C_6)$alkyl, and $R_6$ is linear or branched $(C_1-C_{16})$alkyl;
   $R_2$ is aryl optionally substituted by one or more halogen atoms,
or a pharmaceutically acceptable salt thereof.

2. A method according to claim 1, wherein in said compound or pharmaceutically acceptable salt, stereogenic carbons have a stereochemistry as depicted in formula (I'):

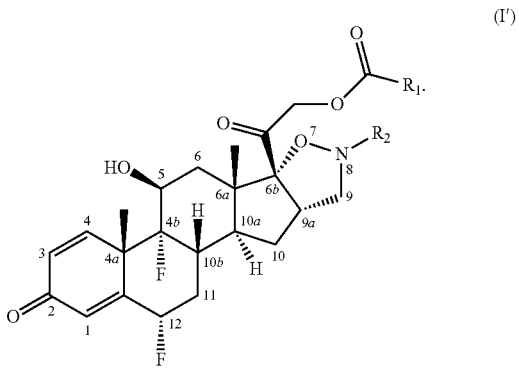

3. A method according to claim 1, wherein $R_1$ is selected from the group consisting of methyl, isopropyl, ethyl, quindecyl, butyl, hexyl, heptadecenyl, methoxy, methylsulfanyl, isobutyl, isopentyl, tertbutyl, methylamino, dimethylamino, phenyl, cyclopropyl, cyclopentyl, methylpropanoxy, benzyl, piridyl, piperazinyl, piperidinyl, pyrrolidinyl, thiazolidinyl, and furyl; and $R_2$ is p-chlorophenyl.

4. A method according to claim 2, wherein $R_1$ is selected from the group consisting of methyl, isopropyl, ethyl, quindecyl, butyl, hexyl, heptadecenyl, methoxy, methylsulfanyl, isobutyl, isopentyl, tertbutyl, methylamino, dimethylamino, phenyl, cyclopropyl, cyclopentyl, methylpropanoxy, benzyl, piridyl, piperazinyl, piperidinyl, pyrrolidinyl, thiazolidinyl, and furyl; and $R_2$ is p-chlorophenyl.

5. A method according to claim 1, wherein said compound or pharmaceutically acceptable salt is a compound selected from the group consisting of:
  isobutyric acid 2-[(4aS,4bR,5S,6aS,6bR,9aS,10aS,10bS, 12S)-8-(4-chloro-phenyl)-4b,12-difluoro-5-hydroxy-4a,6a-dimethyl-2-oxo-2,4a,4b,5,6,6a,8,9,9a,10,10a, 10b,11,12-tetradecahydro-7-oxa-8-aza-pentaleno[2,1-a]phenanthren-6b-yl]-2-oxo-ethyl ester;
  propionic acid 2-[(4aS,4bR,5S,6aS,6bR,9aS,10aS,10bS, 12S)-8-(4-chloro-phenyl)-4b,12-difluoro-5-hydroxy-4a,6a-dimethyl-2-oxo-2,4a,4b,5,6,6a,8,9,9a,10,10a, 10b,11,12-tetradecahydro-7-oxa-8-aza-pentaleno[2,1-a]phenanthren-6b-yl]-2-oxo-ethyl ester;
  hexadecanoic acid 2-[(4aS,4bR,5S,6aS,6bR,9aS,10aS, 10bS,12S)-8-(4-chloro-phenyl)-4b,12-difluoro-5-hydroxy-4a,6a-dimethyl-2-oxo-2,4a,4b,5,6,6a,8,9,9a,10, 10a,10b,11,12-tetradecahydro-7-oxa-8-aza-pentaleno[2,1-a]phenanthren-6b-yl]-2-oxo-ethyl ester;
  octadec-9-enoic acid 2-[(4aS,4bR,5S,6aS,6bR,9aS,10aS, 10bS,12S)-8-(4-chloro-phenyl)-4b,12-difluoro-5-hydro xy-4a,6a-dimethyl-2-oxo-2,4a,4b,5,6,6a,8,9,9a, 10,10a,10b,11,12-tetradecahydro-7-oxa-8-aza-pentaleno[2,1-a]phenanthren-6b-yl]-2-oxo-ethyl ester;
  pentanoic acid 2-[(4aS,4bR,5S,6aS,6bR,9aS,10aS,10bS, 12S)-8-(4-chloro-phenyl)-4b,12-difluoro-5-hydroxy-4a,6a-dimethyl-2-oxo-2,4a,4b,5,6,6a,8,9,9a,10,10a, 10b,11,12-tetradecahydro-7-oxa-8-aza-pentaleno[2,1-a]phenanthren-6b-yl]-2-oxo-ethyl ester;
  acetic acid 2-[(4aS,4bR,5S,6aS,6bR,9aS,10aS,10bS, 12S)-8-(4-chloro-phenyl)-4b,12-difluoro-5-hydroxy-4a,6a-dimethyl-2-oxo-2,4a,4b,5,6,6a,8,9,9a,10,10a, 10b,11,12-tetradecahydro-7-oxa-8-aza-pentaleno[2,1-a]phenanthren-6b-yl]-2-oxo-ethyl ester;
  benzoic acid 2-[(4aS,4bR,5S,6aS,6bR,9aS,10aS,10bS, 12S)-8-(4-chloro-phenyl)-4b,12-difluoro-5-hydroxy-4a,6a-dimethyl-2-oxo-2,4a,4b,5,6,6a,8,9,9a,10,10a, 10b,11,12-tetradecahydro-7-oxa-8-aza-pentaleno[2,1-a]phenanthren-6b-yl]-2-oxo-ethyl ester;
  methyl carbonate (Methyl formate) 2-[(4aS,4bR,5S,6aS, 6bR,9aS,10aS,10bS,12S)-8-(4-chloro-phenyl)-4b,12-difluoro-5-hydroxy-4a,6a-dimethyl-2-oxo-2,4a,4b,5,6, 6a,8,9,9a,10,10a,10b,11,12-tetradecahydro-7-oxa-8-aza-pentaleno[2,1-a]phenanthren-6b-yl]-2-oxo-ethyl ester);
  S-methyl carbonothioate (or S-methyl methanethioate) 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a] phenanthren-6b-yl]-2-oxo-ethyl ester;
  3-methylbutanoic acid 2-[(4aS,4bR,5S,6aS,6bR,9aS, 10aS,10bS,12S)-8-(4-chloro-phenyl)-4b,12-difluoro-5-hydroxy-4a,6a-dimethyl-2-oxo-2,4a,4b,5,6,6a,8,9, 9a,10,10a,10b,11,12-tetradecahydro-7-oxa-8-aza-pentaleno[2,1-a]phenanthren-6b-yl]-2-oxo-ethyl ester;
  pivalic acid 2-[(4aS,4bR,5S,6aS,6bR,9aS,10aS,10bS, 12S)-8-(4-chloro-phenyl)-4b,12-difluoro-5-hydroxy-4a,6a-dimethyl-2-oxo-2,4a,4b,5,6,6a,8,9,9a,10,10a, 10b,11,12-tetradecahydro-7-oxa-8-aza-pentaleno[2,1-a]phenanthren-6b-yl]-2-oxo-ethyl ester;
  2-phenylacetic acid 2-[(4aS,4bR,5S,6aS,6bR,9aS,10aS, 10bS,12S)-8-(4-chloro-phenyl)-4b,12-difluoro-5-hydroxy-4a,6a-dimethyl-2-oxo-2,4a,4b,5,6,6a,8,9,9a,10, 10a,10b,11,12-tetradecahydro-7-oxa-8-aza-pentaleno [2,1-a]phenanthren-6b-yl]-2-oxo-ethyl ester;
  furan-2-carboxylic acid 2-[(4aS,4bR,5S,6aS,6bR,9aS, 10aS,10bS,12S)-8-(4-chloro-phenyl)-4b,12-difluoro-5-hydroxy-4a,6a-dimethyl-2-oxo-2,4a,4b,5,6,6a,8,9, 9a,10,10a,10b,11,12-tetradecahydro-7-oxa-8-aza-pentaleno[2,1-a]phenanthren-6b-yl]-2-oxo-ethyl ester;
  cyclopentane-carboxylic acid 2-[(4aS,4bR,5S,6aS,6bR, 9aS,10aS,10bS,12S)-8-(4-chloro-phenyl)-4b,12-difluoro-5-hydroxy-4a,6a-dimethyl-2-oxo-2,4a,4b,5,6,6a, 8,9,9a,10,10a,10b,11,12-tetradecahydro-7-oxa-8-aza-pentaleno[2,1-a]phenanthren-6b-yl]-2-oxo-ethyl ester;
  cyclopropane-carboxylic acid 2-[(4aS,4bR,5S,6aS,6bR, 9aS,10aS,10bS,12S)-8-(4-chloro-phenyl)-4b,12-difluoro-5-hydroxy-4a,6a-dimethyl-2-oxo-2,4a,4b,5,6,6a, 8,9,9a,10,10a,10b,11,12-tetradecahydro-7-oxa-8-aza-pentaleno[2,1-a]phenanthren-6b-yl]-2-oxo-ethyl ester;
  isonicotinic acid 2-[(4aS,4bR,5S,6aS,6bR,9aS,10aS, 10bS,12S)-8-(4-chloro-phenyl)-4b,12-difluoro-5-hydroxy-4a,6a-dimethyl-2-oxo-2,4a,4b,5,6,6a,8,9,9a,10, 10a,10b,11,12-tetradecahydro-7-oxa-8-aza-pentaleno [2,1-a]phenanthren-6b-yl]-2-oxo-ethyl ester;
  isobutyl methyl carbonate 2-[(4aS,4bR,5S,6aS,6bR,9aS, 10aS,10bS,12S)-8-(4-chloro-phenyl)-4b,12-difluoro-5-hydroxy-4a,6a-dimethyl-2-oxo-2,4a,4b,5,6,6a,8,9, 9a,10,10a,10b,11,12-tetradecahydro-7-oxa-8-aza-pentaleno[2,1-a]phenanthren-6b-yl]-2-oxo-ethyl ester;
  hexyl carbonate 2-[(4aS,4bR,5S,6aS,6bR,9aS,10aS,10bS, 12S)-8-(4-chloro-phenyl)-4b,12-difluoro-5-hydroxy-4a,6a-dimethyl-2-oxo-2,4a,4b,5,6,6a,8,9,9a,10,10a, 10b,11,12-tetradecahydro-7-oxa-8-aza-pentaleno[2,1-a]phenanthren-6b-yl]-2-oxo-ethyl ester);
  dimethyl 2[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a] phenanthren-6b-yl]-2-oxo-ethyl carbamate;
  methyl 2-[(4aS,4bR,5S,6aS,6bR,9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno [2,1-a] phenanthren-6b-yl]-2-oxo-ethyl carbamate;
  piperazine-1-carboxylic acid 2-[(4aS,4bR,5S,6aS,6bR, 9aS,10aS,10bS,12S)-8-(4-chloro-phenyl)-4b,12-difluoro-5-hydroxy-4a,6a-dimethyl-2-oxo-2,4a,4b,5,6,6a, 8,9,9a,10,10a,10b,11,12-tetradecahydro-7-oxa-8-aza-pentaleno[2,1-a]phenanthren-6b-yl]-2-oxo-ethyl ester;
  thiazolidine-4-carboxylic acid 2-[(4aS,4bR,5S,6aS,6bR, 9aS,10aS,10bS,12S)-8-(4-chloro-phenyl)-4b,12-difluoro-5-hydroxy-4a,6a-dimethyl-2-oxo-2,4a,4b,5,6,6a, 8,9,9a,10,10a,10b,11,12-tetradecahydro-7-oxa-8-aza-pentaleno[2,1-a]phenanthren-6b-yl]-2-oxo-ethyl ester;
  proline, 2-[(4aS,4bR,5S,6aS,6bR,9aS,10aS,10bS,12S)-8-(4-chloro-phenyl)-4b,12-difluoro-5-hydroxy-$4^a$,$6^a$-dimethyl-2-oxo-2,4a,4b,5,6,$6^a$,8,9,$9^a$,10,$10^a$,10b,11,12-tetradecahydro-7-oxa-8-aza-pentaleno[2,1-a] phenanthren-6b-yl]-2-oxo-ethyl ester; and
  piperidine-4-carboxylic acid, 2-[(4aS,4bR,5S,6aS,6bR, 9aS,10aS,10bS,12S)-8-(4-chloro-phenyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester; or a pharmaceutically acceptable salt of said compound.

* * * * *